United States Patent
Mensch et al.

(10) Patent No.: US 10,849,682 B2
(45) Date of Patent: Dec. 1, 2020

(54) FORCEPS INCLUDING A DOUBLE BIASED HANDLE LATCH

(71) Applicant: GYRUS ACMI, INC., Southborough, MA (US)

(72) Inventors: John R. Mensch, Plymouth, MN (US); Riyad Moe, Madison, WI (US); Kester J Batchelor, Mound, MN (US)

(73) Assignee: Gyrus Acmi, Inc., Southborough, MA (US)

( * ) Notice: Subject to any disclaimer, the term of this patent is extended or adjusted under 35 U.S.C. 154(b) by 149 days.

(21) Appl. No.: 15/941,590

(22) Filed: Mar. 30, 2018

(65) Prior Publication Data

US 2019/0298440 A1     Oct. 3, 2019

(51) Int. Cl.
*A61B 18/14* (2006.01)
*A61B 17/29* (2006.01)

(52) U.S. Cl.
CPC .. *A61B 18/1447* (2013.01); *A61B 2017/2925* (2013.01); *A61B 2017/2946* (2013.01);
(Continued)

(58) Field of Classification Search
CPC ............ A61B 17/2833; A61B 17/2837; A61B 17/2841; A61B 17/235; A61B 17/2909; A61B 2017/291–2925; A61B 2017/2845; A61B 2017/2946; A61B 18/1447; A61B 18/085; A61B 18/1442; A61B 18/1445;
(Continued)

(56) References Cited

U.S. PATENT DOCUMENTS

| 1,198,958 A | 9/1916 | Risley |
| 2,042,985 A | 6/1936 | Gardella |

(Continued)

FOREIGN PATENT DOCUMENTS

| EP | 0392548 A1 | 10/1990 |
| EP | 0908152 A1 | 4/1999 |

OTHER PUBLICATIONS

Potentially Related U.S. Appl. No. 15/941,128, filed Mar. 30, 2018.
(Continued)

*Primary Examiner* — Katherine M Shi
*Assistant Examiner* — Alyssa M Keane
(74) *Attorney, Agent, or Firm* — Schwegman Lundberg & Woessner, P.A.

(57) ABSTRACT

A surgical device comprising: a closure assembly including: (a) a movement unit configured to be connected to a movable member, the movement unit including: (i) one or more bars; (ii) one or more bar biasing members in communication with the movement unit and moving the one or more bars; (b) a latch unit configured to be connected to a ground member, the latch unit including: (i) one or more hook latches that selectively receive the one or more bars, and (ii) one or more latch biasing members in communication with the one or more hook latches to selectively move the one or more hook latches; wherein all or a portion of the latch unit is movable relative to the ground member and all or a portion of the movement unit is movable relative to the movable member, and the latch unit and the movement unit are movable relative to each other when the latch unit and the movement unit are in contact.

18 Claims, 14 Drawing Sheets

(52) U.S. Cl.
CPC .............. *A61B 2018/1455* (2013.01); *A61B 2018/1462* (2013.01)

(58) Field of Classification Search
CPC .... A61B 2018/1455; A61B 2018/1462; A61B 10/06; A61B 1/00066; A61B 1/0052; B25B 7/14; B25B 7/16
USPC .................................... 606/51–52, 205–209
See application file for complete search history.

(56) References Cited

U.S. PATENT DOCUMENTS

| | | | |
|---|---|---|---|
| 2,214,984 A | 9/1940 | Bachmann | |
| 2,381,084 A | 8/1945 | Slad | |
| 2,894,424 A | 7/1959 | Vaughan | |
| 3,189,374 A | 6/1965 | Mertes | |
| 3,399,583 A | 9/1968 | Hall | |
| 3,465,621 A | 9/1969 | Ladd | |
| 3,643,663 A | 2/1972 | Sutter | |
| 3,694,015 A | 9/1972 | Gley | |
| 3,699,632 A | 10/1972 | Anhalt | |
| 3,819,282 A | 6/1974 | Schultz | |
| 3,913,586 A | 10/1975 | Baumgarten | |
| 4,215,884 A | 8/1980 | Little | |
| 4,318,313 A | 3/1982 | Tartaglia | |
| 4,449,022 A | 5/1984 | Uno et al. | |
| 4,494,543 A | 1/1985 | Hart | |
| 4,792,165 A | 12/1988 | Nishimura | |
| 5,104,397 A | 4/1992 | Vasconcelos et al. | |
| 5,176,702 A | 1/1993 | Bales et al. | |
| 5,211,655 A | 5/1993 | Hasson | |
| 5,358,292 A | 10/1994 | Van Wiebe et al. | |
| 5,425,743 A | 6/1995 | Nicholas | |
| 5,498,039 A | 3/1996 | Bivens | |
| 5,499,998 A | 3/1996 | Meade | |
| 5,735,849 A | 4/1998 | Baden et al. | |
| 5,884,954 A | 3/1999 | Trozera | |
| 6,050,996 A | 4/2000 | Schmaltz et al. | |
| 6,056,333 A | 5/2000 | Wach | |
| 6,247,733 B1 | 6/2001 | Weiland | |
| 6,585,735 B1 | 7/2003 | Frazier et al. | |
| 6,669,250 B1 | 12/2003 | St. Louis | |
| 6,799,705 B1 | 10/2004 | Lutoslawski | |
| 7,115,139 B2 | 10/2006 | McClurken et al. | |
| 7,118,587 B2 | 10/2006 | Dycus et al. | |
| 7,150,749 B2 | 12/2006 | Dycus et al. | |
| 7,201,411 B2 | 4/2007 | Bella et al. | |
| 7,232,440 B2 | 6/2007 | Dumbauld et al. | |
| 7,766,910 B2 | 8/2010 | Hixson et al. | |
| 7,793,995 B2 | 9/2010 | King et al. | |
| 7,802,856 B2 | 9/2010 | Hashemi et al. | |
| 8,109,582 B2 | 2/2012 | Dubach | |
| 8,246,094 B2 | 8/2012 | Long et al. | |
| 8,328,170 B2 | 12/2012 | Wasinger | |
| 8,398,620 B2 | 3/2013 | Bacher et al. | |
| 8,945,175 B2 | 2/2015 | Twomey | |
| 9,452,011 B2 | 9/2016 | Batchelor et al. | |
| 9,851,741 B2 | 12/2017 | Lamser et al. | |
| 2002/0016609 A1 | 2/2002 | Wensel et al. | |
| 2006/0190035 A1 | 8/2006 | Hushka et al. | |
| 2006/0208506 A1 | 9/2006 | Kern et al. | |
| 2008/0154300 A1 | 6/2008 | Jabbour | |
| 2011/0301637 A1 | 12/2011 | Kerr et al. | |
| 2012/0109187 A1 | 5/2012 | Gerhardt, Jr. et al. | |
| 2012/0184989 A1 | 7/2012 | Twomey | |
| 2012/0184990 A1 | 7/2012 | Twomey | |
| 2012/0191091 A1 | 7/2012 | Allen | |
| 2013/0066317 A1 | 3/2013 | Evans et al. | |
| 2013/0178852 A1 | 7/2013 | Allen, IV et al. | |
| 2013/0325057 A1 | 12/2013 | Larson et al. | |
| 2014/0135805 A1 | 5/2014 | Windgassen et al. | |
| 2014/0236156 A1 | 8/2014 | Arlettaz et al. | |
| 2014/0276795 A1 | 9/2014 | Batchelor et al. | |
| 2015/0331443 A1 | 11/2015 | Lamser et al. | |
| 2016/0051275 A1 | 2/2016 | Batchelor et al. | |
| 2016/0338763 A1 | 11/2016 | Allen, IV et al. | |
| 2017/0367752 A1* | 12/2017 | Boudreaux ........ | A61B 18/1445 |

OTHER PUBLICATIONS

Potentially Related U.S. Appl. No. 15/941,205, filed Mar. 30, 2018.
Potentially Related U.S. Appl. No. 15/967,491, filed Apr. 30, 2018.
Potentially Related U.S. Appl. No. 14/706,146, filed May 7, 2015, published as 9,851,741 on Dec. 26, 2017.
Olympus, HALO Cutting Forceps (http://www.olympusamerica.com/msg_section/envision/oneoffpages/files/Halo_PKS_Brochure.pdf) (Last Accessed May 14, 2018).

* cited by examiner

US 10,849,682 B2

FORCEPS INCLUDING A DOUBLE BIASED HANDLE LATCH

FIELD

The present teachings relate to forceps with a first jaw and a second jaw that are movable relative to each other and a movement unit and a latch unit that when connected prevent movement of the first jaw to the second jaw, and specifically a movement unit and a latch unit that are separately biasable relative to each other.

BACKGROUND

Generally, forceps may be utilized for laparoscopic surgery or open surgery. The forceps may be used to control delicate movements inside a patient. These forceps may be used to grip an anatomical feature. The forceps may include a gripping assembly or a cutting assembly. The forceps may include electrical energy for use in the gripping assembly, the cutting assembly, or both. The forceps have a pair of opposed resilient jaws that are closed against each other or a cutting blade. The jaws of the forceps may be locked together so that the surgeon may lock the forceps on a feature of interest while the surgeon works on a different anatomical feature or uses a different instrument. Examples of some latches or forceps including locks may be found in U.S. Pat. Nos. 5,104,397; 5,425,743; 6,056,333; 6,247,733; 7,118,587; 7,802,856; 8,945,175; and 9,851,741 and U.S. Patent Application Publication No.: 2013/0066317; 2014/0276795; 2015/0331443; 2016/0051275 all of which are incorporated by reference herein in their entirety for all purposes. During locking of the arms to each other the user may have to regrip one or more times in order to lock the jaws together. Furthermore, during releasing the user may be required to manipulate the jaws one or more times in order for the lock to release the jaws.

It would be attractive for the forceps to include two or more springs that bias two or more separate parts so that each of the parts are biased relative to each other. What is needed is a latch unit that is positively biased and a movement unit that is positively biased. What is needed is a latch unit that is positively biased in a home position, a locked position, and an unlocked position. It would be attractive to have movement unit that is positively biased in a home position, a locked position, and an unlocked position. What is needed is a closure assembly include a latch unit, a bar unit, or both that are pre-loaded against a stop so that the closure assembly can be reliably located, locked, unlocked, or a combination thereof.

SUMMARY

The disclosure meets one or more of the needs by providing: a surgical device comprising: a closure assembly including: (a) a movement unit configured to be connected to a movable member, the movement unit including: (i) one or more bars; (ii) one or more bar biasing members in communication with the movement unit and moving the one or more bars; (b) a latch unit configured to be connected to a ground member, the latch unit including: (i) one or more hook latches that selectively receive the one or more bars, and (ii) one or more latch biasing members in communication with the one or more hook latches to selectively move the one or more hook latches; wherein all or a portion of the latch unit is movable relative to the ground member and all or a portion of the movement unit is movable relative to the movable member, and the latch unit and the movement unit are movable relative to each other when the latch unit and the movement unit are in contact.

The present teachings provide a surgical device comprising: a closure assembly including: (a) a movement unit including: (i) one or more bars; (ii) one or more bar biasing members in communication with the one or more bars to selectively move the one or more bars; and (iii) one or more bar stops that maintain the one or more bar biasing members with a pre-load when the one or more bars are in a home position; (b) a latch unit including: (i) one or more hook latches that selectively receive the one or more bars, (ii) one or more latch biasing members in communication with the one or more hook latches to selectively move the one or more hook latches; and (iii) one or more latch stops that maintain the one or more latch biasing members with a pre-load when the one or more latch stops are in a home position; wherein the latch unit and the movement unit are movable relative to each other when the latch unit and the movement unit are in contact.

The teachings herein provide forceps to include two or more springs that bias two or more separate parts so that each of the parts are biased relative to each other. The teachings herein provide a latch unit that is positively biased and a movement unit that is positively biased. The teachings herein provide a latch unit that is positively biased in a home position, a locked position, and an unlocked position. The teachings herein provide a movement unit that is positively biased in a home position, a locked position, and an unlocked position. What is needed is a closure assembly include a latch unit, a bar unit, or both that are pre-loaded against a stop so that the closure assembly can be reliably located, locked, unlocked, or a combination thereof.

DETAILED DESCRIPTION

Figure 1:
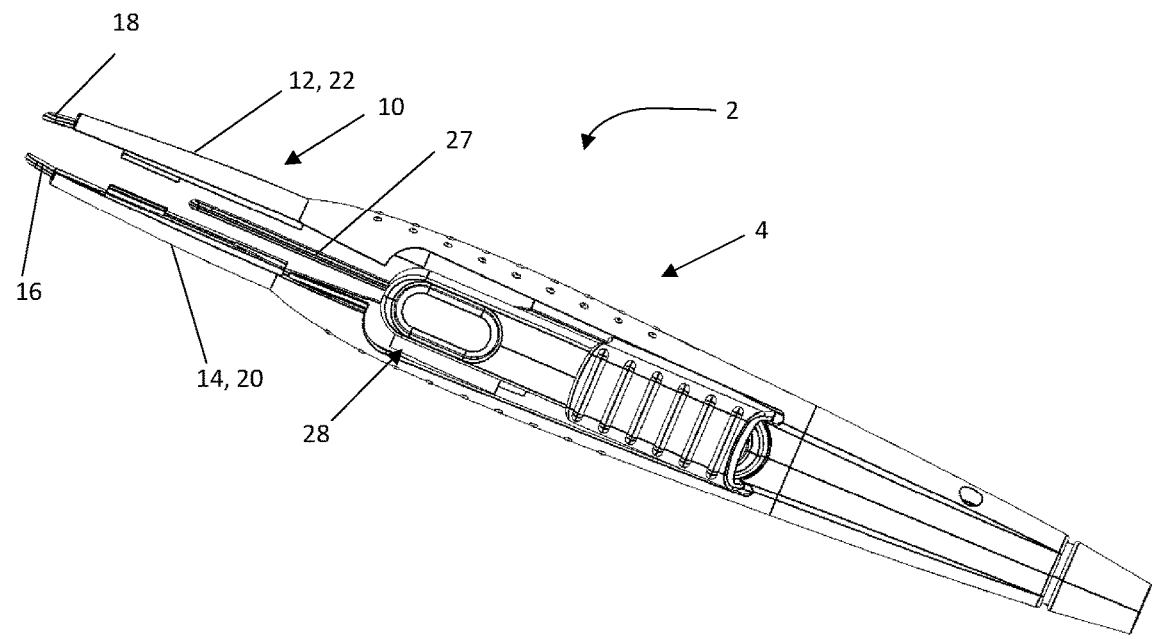
FIG. 1 is a perspective view of an electrosurgical device having a latching assembly.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings relate to a closure assembly that connects two or more members together and prevents movement of the two members relative to each other. The closure assembly may connect a movable member to a ground member or connect two movable members together. The closure assembly may have a latch unit and a bar unit that are both displaceable relative to each other to lock and unlock the closure assembly. The closure assembly may prevent movement of a door (e.g., movable member) relative to storage space (e.g., ground member). The closure assembly may be part of a hand-held device, pliers, clamps, or a combination thereof. The closure assembly may fit entirely within a hand piece, a housing, a handle, or a combination thereof that fits within a hand of a user. The closure assembly may move from a first side of a hand piece, a housing, a handle, or a combination thereof to a second side. The closure assembly may be part of a drawer, cabinet, bin, a door, or a combination thereof. Preferably, the closure assembly is part of a surgical device and prevents arms that control forceps from moving relative to each other.

The present teachings relate to a surgical device. The surgical device may be a non-electrical device (i.e., may only provide mechanical functions such as mechanical cutting or gripping). Preferably, the surgical device is an electrosurgical device. The electrosurgical device may provide one or more therapy currents. Preferably, the electrosurgical device provides two or more therapy currents (e.g., monopolar power and bipolar power). A therapy current may pass between the jaws (e.g., bipolar power). A therapy current may pass from a jaw to a blade or vice versa. A therapy current (e.g., monopolar power) may pass from a blade to a remote electrode (e.g., ground pad). The electrosurgical device may apply power before, after, or simultaneously with a mechanical technique (e.g., gripping or cutting). When power is applied an anatomical feature may be cut, cauterized, sealed, coagulated, or a combination thereof. The electrosurgical device may include a distal end and a proximal end. The distal end may include a portion of a forceps device (e.g., jaws, blade, or both). The distal end may be a portion of the surgical device that is farthest from a user. The proximal end may be a portion a user grips (e.g., hand piece or housing) or a portion closest to a user.

The present teachings provide a forceps device. The forceps may function to grip an object. Preferably, the forceps may be used during surgery to grip a feature of interest including: a part of a body, an anatomical feature, tissue, veins, arteries, or a combination thereof. The forceps may assist in applying a therapy current to a feature of interest. The forceps may move between a first position (e.g., release position) and a second position (e.g., gripping position). The forceps may be fully closed in a full-pull position or partially closed in a partial pull position. The forceps may function to be used in surgery, for example laparoscopic surgery. The forceps may be used with or without power. A therapy current may be passed from one jaw to a second jaw when tissue is located between the jaws and the therapy current may coagulate blood, cauterize, cut, or a combination thereof. In another example, a therapy current may be passed from one or more of the jaws and/or a blade to a remote electrode (e.g., a return pad). The forceps may include a first working arm with a jaw and a second working arm with a jaw. The forceps may be comprised of parts needed to perform the recited functions and may include generally, a stylet (e.g., a tubular member, a hollow tube, or an assembly of tubes), a hand piece, one or more operable mechanisms used to actuate the stylet, two or more jaws, two or more working arms, or a combination thereof.

The two or more working arms may function to move towards and away from each other to assist a user in gripping a feature of interest. The two or more working arms may be directly biased towards each other by a user. Preferably, the two or more working arms are biased towards each other by a stylet or tube moving over the arms (e.g., distally) so that the arms are moved together. The two or more working arms may be moved towards each other by being retracted into a stylet or tube. The two or more arms may be moved towards each other by direct pressure being applied to one or both of the working arms. The working arms may be solid and rotate about a pivot. The working arms may be a wire that is shaped to create a working arm, a jaw, or both. The working arms may have one or more rods, one or more wires, or both that extend into a stylet and connect to the hand piece. Each of the two or more working arms may include a jaw.

The two or more opposing jaws may function to create a gripping force, grip a feature of interest, or both. The two or more opposing jaws may move towards each other to create a gripping force, to grip a feature of interest, or both. The two or more opposing jaws may function to be used to grip or clamp an item of interest for cutting or applying a bipolar energy source. Preferably, the two or more opposing jaws may be one jaw structure with another mirror image opposing jaw structure (i.e., identical) that when forced together may create a gripping function. The two opposing jaws may be any two or more structures that may be movable relative to each other for perform a gripping function. The two opposing jaws may be any structures that may allow one jaw to be static and one jaw to be movable or any combination thereof. The jaws may be a gripping portion of a working arm. The two opposing jaws may be formed of two wires that are shaped to have a generally "U" shaped end. The two opposing jaws may be made of any material so that the two opposing jaws may be used to create a gripping force. The two opposing jaws may be made of a flexible material, resilient material, rigid stainless steel, a plastically deformable material, an elastically deformable material, or a combination thereof. The jaws, working arms, or both may be substantially solid but may have some elasticity. The two opposing jaws may be made of a material that conducts electricity. The two opposing jaws may include a channel (e.g., a blade track) to allow for a cutting instrument to be inserted while retaining functionality of the two or more opposing jaws. The two opposing jaws may be used to apply electricity to a feature of interest that may be gripped by the two opposing jaws. The two opposing jaws may be a first jaw and a second jaw. The first jaw may be movable relative to the second jaw, or vice versa. The first jaw and second jaw may be longitudinally movable relative to each other. Preferably, the first jaw and second jaw longitudinally move in unison. The first jaw and second jaw may be longitudinally static. The first jaw and second jaw may move about a pivot towards and away from each other. The two opposing jaws may be moved between a release position and a retract position by retraction of one of the one or more jaw shafts, movement of the one or more tubular members towards the distal end, or both along an axis of the one or more tubular members; an application of force by a user; or a combination thereof. The two opposing jaws may have laterally extending arcuate sections at the proximal end (e.g., heel of the jaw) of the jaws that protrude out from the distal end of the tubular member, while one or more jaw support rods extend into the tubular member. A closure assembly may lock the two opposing jaws together, lock the two opposing jaws on tissue, lock the two opposing jaws on a blade, or a combination thereof.

The blade may function to cut a feature of interest. The blade may be any cutting tool that may be used in surgery, for example laparoscopic surgery or open surgery. The blade may be any cutting device that may be extended and retracted through the stylet or between the first working arm and the second working arm. The blade may extend along a stylet. The blade may be made of any material that may be sharpened; is strong enough to cut a feature of interest; is biocompatible; that may conduct electricity; or a combination thereof. The blade may mechanically cut, electrically cut, or both. The blade may be substantially solid along a length of the blade. The blade may be sufficiently small so that the blade may be housed in the tubular member, tube, or both of a stylet during movement, insertion, or both. The blade may be extended into, and retracted from, a channel in the two opposing jaws. The distal end of the blade may have a shaped edge. The blade may extend flush with or distal of the jaws. The blade may conduct power. The blade may conduct a therapy current. The blade may conduct bipolar energy, monopolar energy, or both. The proximal end of the blade may be attached to a blade support rod. The blade may be connected to a closure assembly that restricts movement of the blade or assists in moving the blade. All or a portion of the blade may extend out of the stylet, between and past the jaws, or both to cut a feature of interest.

The stylet as discussed herein may include one or more tubular members or may be a tubular member (i.e., tube). The stylet may be a neck that connects jaws, a blade, or both to a hand piece. The stylet may include one or more tubes, one or more shafts, or both that may extend through the tubes. The stylet may include a tubular member and an inner tube. The stylet may be a hollow tube with one or more shafts extending through the hollow tube. The stylet may function to extend into a patient during a surgical procedure so that a user (i.e., surgeon) can perform one or more surgical procedures. The stylet may be flexible so that the stylet may be moved within a patient. Preferably, the stylet may be substantially rigid so that the stylet may be moved to a desired location. The stylet includes a distal end and a proximal end. The distal end may be an end of the stylet that is located farthest from the hand piece (e.g., the end of the stylet that is inserted into a patient). The proximal end of the stylet may be the end of the tube located proximate to the user, in the hand piece, or both. The stylet and its components may be made of any biocompatible material, for example, stainless steel, plastic, a synthetic material, a natural material, or a combination thereof. The tube subassembly may include one or more tubes, one or more inner tubes, one or more outer tubes, one or more gripping assemblies, one or more cutting assemblies, one or more rotation mechanisms, one or more operable mechanisms, one or more camming shafts, one or more guides, one or more spacing members, one or more jaw shafts, one or more blade shafts, or a combination thereof. Preferably, the stylet includes at least an outer tube that extend from a hand piece to a distal end.

The one or more outer tubes may function to close the jaws, bias the jaws, or both. The one or more outer tubes may function to house one or more jaws, one or more blades, or both. The one or more outer tubes may be axially static. The one or more outer tubes may axially move to open and close the jaws. The one or more jaws may overrun the inner tube, the jaws, the arcuate sections, or a combination thereof to bias the jaws towards each other. The one or more inner tubes may function to create a point of contact for one or more jaws. The one or more inner tubes may form a connection point, include a connection feature (e.g., a pin, bolt, screw, rivet, or a combination thereof) for one or more jaws. The one or more inner tubes may be part of a tubular member or a stylet. The one or more inner tubes may be movable relative to an outer tube. The one or more forceps may be free of any tubes or tubular members. The one outer tubes of the stylet may assist in connecting the jaws, the blade, or both to the hand piece.

The hand piece may be an assembly of parts or housing structures capable of forming a structure with a cavity that a user holds in their hand. The hand piece may function to be gripped by a user. When gripped by a user a top or upper portion of the handpiece may be located up relative to a user's hand and the bottom or lower portion may be located down relative to a user's hand. Thus, up may include the one or more button, a region the stylet extends from, or both, and down may be where a cord extends out of the hand piece. The hand piece may function to hold or encapsulate one or more or a plurality of components of the surgical device. The forceps may extend from the hand piece and may be actuated by one or more operable mechanisms located within the hand piece. The forceps may be actuated by direct pressure being applied to one or both of the jaws that extend from the hand piece so that the jaws are moved towards or away from each other (e.g., laterally moved). The forceps may be actuated by movement of a trigger that is connected to the hand piece. The hand piece and the trigger may be biased apart. A bias device may extend between the hand piece and the trigger so that a gap is located between the hand piece and the trigger. The hand piece and the trigger may be biased apart. A bias device may extend between the hand piece and the trigger so that a gap is located between the hand piece and the trigger. A bias device may be located along the stylet, within the hand piece, in communication with a part that axially moves so that the working arms are moved together, or a combination thereof. The bias device may be a bias device taught herein including those taught in U.S. Pat. No. 9,851,741 regarding a compression spring or element 90 or the teachings of U.S. Pat. No. 5,735,849 regarding a torsion spring or element 80 the teachings of which are incorporated by reference herein for all purposes include those regarding how a moveable member is moved relative to a ground member and especially how a trigger is moved relative to a handle. The hand piece may be solid and the first working arm and the second working arm, the first jaw and the second jaw, or both may be biased apart by a bias member. The hand piece may include the latch unit and the trigger may include the movement unit and when the movement unit and the latch unit are not connected together the bias member may move the trigger to form the gap therebetween. A first working arm may include the latch unit and a second working arm may include the movement unit. The forceps may create a sufficient gripping force so that one or more features of interest (e.g., a part of a patient's body) may be manipulated by the gripping assembly, secured by the gripping assembly, or a combination thereof. The forceps may grip and release while being simultaneously rotated about the hand piece. The forceps may be actuated by the actuation mechanism in communication with the forceps or a user directly contacting the forceps. The hand piece may function to form an enclosing structure for all or a portion of the forceps, a gripping portion for the user, a main portion for manipulating the forceps, or a combination thereof. The hand piece may be any device that houses all or a portion of the working assemblies and parts of the forceps. The hand piece may be comprised of one or more housing structures. Preferably, the hand piece is two or more housing structures. The housing structures may be two plastic pieces that connect together to enclose an open space that receives components of the surgical device. The hand piece may be any structure that is gripped by a user. The hand piece may be a ground member. The hand piece may be static. The hand piece may be a ground member that is static when a user applies a pressure so that a movable member is moved relative to the ground member. The hand piece may assist in performing laparoscopic surgery. The hand piece may be ergonomically shaped. The hand piece may be used ambidextrously. The hand piece may form a cavity to house working assemblies of the forceps. The hand piece may be one or more housing structures and preferably two or more housing structures. The hand piece may be any device that includes a recess for receiving one or more components of the forceps. The housing structures may house all or a portion of one or more operable mechanisms, one or more valves, one or more fluid distribution systems, or a combination thereof. The hand piece may house all or a portion of an operable mechanism that causes the jaws to move, the blade to move, the valve to open, the valve to close, all or a portion of a fluid distribution system, or a combination thereof. The hand piece may be made of one or more housings.

The one or more housings may function to form a hand piece, enclose a portion of an operable mechanism, enclose a portion of a stylet, enclose one or more tubes, or a combination thereof. The one or more housings may be a left half and a right half or a top half and a bottom half. The housing may be multiple pieces that are connected together. The housing may be made of plastic. The housing may be a combination of plastic and metal. The housing may provide a stationary part (e.g., ground member) that a user grips while a user moves a trigger (e.g., movable member) to actuate the forceps, a blade, or both. Preferably, the housing is connected to two or more triggers that movably connect to the housing so that upon actuation the jaws, blade, fluid distribution system, or a combination thereof are moved or actuated by one of the two or more triggers. More preferably, the triggers are movable relative to the housing to actuate the jaws, blade, fluid distribution system, or a combination thereof. The housing may be connected to a first jaw, a second jaw, or both jaws of forceps and a direct force may be applied to the housings in order to move the forceps towards or apart from each other. For example, upon a force being applied to the housing the jaws may move towards each other. In another example, upon a force being applied to the housing the jaws may move apart. The housing may be a proximal end (e.g., end closest to a user) and the jaws or blade may be the distal end (e.g., end farthest from a user). The housing may include all or a portion of a closure assembly. Preferably, the housing includes the latch unit. The jaws, blade, fluid distribution system, or a combination thereof may be moved between a first position (release position) and a second position (retract position) by one or more operable mechanisms or direct contact by a user. The housing may have a portion that is a handle that a user grips.

The handle may function to assist in actuation of the forceps, the blade, applying electricity, or a combination thereof. The handle may be gripped by one hand. The handle may be part of the hand piece. The handle may include a lock, a lock plate, all or a portion of a closure assembly, a latch unit, or a combination thereof. The handle may be a proximal end of the surgical device. The handle may extend from a body portion or the hand piece. The handle may extend from an angle relative to the body portion of the hand piece. The handle may be a static member that one or more triggers move relative to. The handle may include a latch unit. The handle may be a ground member that a movable member, a trigger, or both are movable relative to.

The ground member may function to be static and another part (e.g., the movable member) may be moved relative to the ground member. The ground member may form a coordinate system, a reference point for relative motion of other components of the device taught herein, or a center of a coordinate system. The ground member may be connected to or located next to a movable member and function to prevent movement of another component such as forceps or a blade as the movable member moves relative to the ground member. The ground member may be part of a first working arm. The ground member may be a handle, a housing, a hand piece, or a combination thereof. Preferably, the ground member is the handle or hand piece. The ground member may include all or a portion of a closure assembly. Preferably, the ground member may include all of the latch unit. The ground member may receive a portion of a force to assist a movable member in being moved relative to the ground member. The ground member may receive a portion of the movable member to form a locked state.

The movable member may function to move relative to a ground member so that the forceps or blade may be actuated, locked, released, or a combination thereof. The movable member may be biased apart from the ground member (e.g., a bias device may be located between the movable member and the ground member). The movable member may move with or relative to a ground member to lock, unlock, bias, or a combination thereof two or more jaws two or more working arms, a blade, or a combination thereof. The movable member may move to open and close the jaws, move the blade, or both. Preferably, the movable member may be a trigger. More preferably, the movable member may be a cut trigger, a clamp trigger, or both. The movable member may include all or a portion of the closure assembly. Preferably, the movable member may include or be connected to the movement unit. The movable member may move relative to the ground member so that the movement unit moves along a movement path (e.g., prescribed motion). The movable member may rotate about a pivot relative to the ground member, may translate relative to the ground path, may move in a nonlinear or nonrotating movement of a mechanism such as four bar linkage relative to the ground member, or a combination thereof. The movable member may be part of the closure assembly that assists in locking the jaws, the working arms, the surgical device, or a combination thereof.

The closure assembly may function to connect a movable member and a ground member together. The closure assembly may function to lock a first working arm to a second working arm, a first jaw to a second jaw, a blade in an extended state or in a retraced state, or a combination thereof. The closure assembly may be movable between a lockable state and an unlockable state. The closure assembly may lock two items together when the closure assembly is in a locked state. The closure assembly may freely move as the movable member, the ground member, or both move relative to each other or are in an unlockable state. A portion of the closure assembly may be located on or within the movable member, the ground member, the movement unit, the latch unit, or a combination thereof. Preferably, the closure assembly includes a movement unit and a latch unit.

More preferably, the closure assembly may be part of a movable member and a ground member and the movable member may be a trigger and the ground member may be a handle.

The one or more triggers function to be an input to an operable mechanism that moves one or both jaws, one or both working arms, one or more blades, or a combination thereof. The one or more triggers may function to be an input that directly moves one or more working arms, a blade, or both. The one or more triggers may be a movable member or a ground member. Preferably, the triggers are a movable member and the ground is a handle or hand piece. The one or more triggers as discussed herein may be a lever, handle, link, or a combination thereof. The one or more triggers may be a cut trigger, a clamp trigger, an activation switch, or a combination thereof that when actuated inputs movement into an operable mechanism so that the operable mechanism provides an output. If the triggers are a lever, the lever is a rigid member that turns on a pivot. The cut lever, the clamp lever, or both may function to move one or more jaws, one or more blades, a jaw support rod, a blade support rod, a second link, one or more valves, or a combination thereof. The cut lever, the clamp lever, or both may extend between a release position ((e.g., a start position) in a forward stroke direction) and a retract position ((e.g., a full pull position where the jaws are closed, the blade is extended, or both) in a return stroke direction). The cut lever and the clamp lever may be individually biased apart from the handle, the hand piece, or both. The cut lever, the clamp lever, or both as they extend from a start position (or home position) to a full pull-position may close jaws, activate a functional element, extend a blade, or a combination thereof. For example, as the clamp trigger is moved in a forward stroke direction, the clamp trigger may begin to close the jaws and as the jaws close a closure assembly may simultaneously be closed such that the jaws are locked together. The one or more triggers may assist in moving the one or more blades, one or more working arms or both from a closed state to an open state when the triggers move in a return stroke direction. The one or more triggers may be part of the closure assembly, part of a movement unit, or both. Preferably, the one or more triggers carry the movement unit so that the movement unit when in communication with the latch unit may restrict movement of the trigger.

The movement unit may be integrally connected to a movable member, a trigger, or both. The movement unit may extend from the movable member towards the ground member and even into the ground member. A portion of the movement unit may be located within the movement member. The movement unit may move with the movement member. Preferably, the movement unit moves with the movement member and all or a portion of the movement unit moves with the movement member. The movement unit may move in along a longitudinal axis of the movement member. The movement unit may move in a prescribed motion relative to the ground member. The prescribed movement may be a linear motion, an arcuate movement, or a combination of both. The prescribed motion may overlap in a first direction and a second direction. For example, the bar extending along the prescribed motion in a forward stroke is the same movement location when the bar extends along the prescribed motion in the return stroke. The movement unit may rotate about a pivot so that the movement unit travels back and forth along a constant path (e.g., a prescribed motion). The movement unit may extend cantilever from a movable member, a trigger, or both. The movement unit may extend into contact with a latch unit to form a locked state.

The movement unit may move in relationship to the latch unit to form an unlocked state. The movement unit may move in a prescribed motion at all times and the latch unit may move relative to the movement unit so that a lockable state, an unlockable state, a locked state, an unlocked state, or a combination thereof may be formed. The movement unit may include one or more bar arms, one or more bars, a bar movement frame, a bar frame, a pivot, a bar stop, one or more bar biasing members, or a combination thereof.

The bar unit functions to connect to a latch unit. The bar unit may include one or more bars that connect to one or more hook latches. The bar unit may be part of or included within a movable member. All or a portion of a bar unit may be movable relative to the movable member, along the movable member, or both. Preferably, the bar unit and the movement unit are the same. The bar unit may include one or more bars, one or more bar frames, one or more bar movement units or a pivot, one or more bar biasing members, one or more bar stops, or a combination thereof.

The one or more bar frames may function to connect the movement unit, the bar unit, or both to a member and preferably to a movement unit. The one or more bar frames may ground all or portion of the movement unit. The bar frame may be part of the trigger, the movement unit, or both. The bar frame may be connected to the trigger, the movement unit, or both. The one or more bar frames may be connected to or include a bar biasing member, a bar stop, a bar movement unit, a pivot, or a combination thereof. The bar frames may include a window that receives all or a portion of the bar movement unit. The window may receive a pin, a connection member, or both. The window may connect to a bar arm so that the bar arm rotates about an axis. The bar frame may include a track. The bar frames may be connected to a pivot. The bar frame may ground the bar movement unit, the pivot, or both. The bar frame may guide a bar movement unit along a trigger, a movement member, or both. The bar frame may house the bar movement unit and the bar arm may extend from the bar frame. The bar frame may ground a bar stop, a bar biasing member, or both. The bar frame may have one or more sidewalls. The one or more sidewalls may guide a bar movement unit, stop a bar movement unit, or both.

The one or more bar movement units may function to permit the bar to move relative to the movement unit, the trigger, the latch unit, or a combination thereof. The one or more bar movement units may be part of the movement unit that moves relative to a movement member, a trigger, a bar frame, or a combination thereof. The bar movement unit may slide along a track of the bar frame. Preferably, the bar movement unit may slide within a window within the bar frame. The bar movement unit may allow the bar to circumnavigate the hook latch. The bar movement unit may be movably connected within the bar frame. The bar movement unit may slide. The bar movement unit may move along a longitudinal axis of the trigger, movement unit, or both. The bar movement unit may connect the bar, the bar arm, or both within a movement unit, a bar frame, or both. The bar frame may be free of a bar movement unit, the bar movement unit may be a pivot, or both.

The one or more pivots may function to permit the bar to move relative to the movement unit, the trigger, the latch unit, or a combination thereof. The one or more pivots may allow for rotatable movement of the bar arm relative to the bar frame, the trigger, the movement member, or a combination thereof. The one or more pivots may allow the bar to circumnavigate the hook latch. The one or more pivots may be an axis. The one or more pivots may be a point of connection between the bar arm and the bar frame. The one or more pivots may allow for rotational movement of the bar arm relative to the bar arm relative to the bar frame. The one or more pivots, the bar movement unit, or both may be connected to or moved by one or more bar biasing members.

The one or more bar biasing members function to move the bar, the movement unit, the bar arm, or a combination thereof. The one or more bar biasing members may function to bias or displace the bar arm, the bar, or both to a home position, a neutral state, into contact with a bar stop, or a combination thereof. The one or more bar biasing members may be a spring, a torsion spring, a compression spring, an elastomeric member, an extension spring, a conical spring, an elastomeric piece, or a combination thereof. The bar biasing members may be the same as a latch biasing member. The teachings herein for the bar biasing member and the latch biasing member may be interchanged. The bar biasing member may expand and contract within movement of the bar arm, the bar, or both. The bar biasing member may be located around an axis. The bar biasing member may be a torsion spring that is compressed, or uncompressed as the bar arm moves relative to the bar frame, the trigger, the movement member, or a combination thereof. The bar biasing member may be a bar arm that extends from a bar frame. The bar biasing member may form a cantilevered connection that supports the bar at an end from the bar frame. The bar biasing member may be a linear piece. The bar biasing member be or include a spring steel, elastomer, plastic, or a combination thereof. The bar biasing member have a home state that is straight. The bar biasing member may extend or be deflected up, down, or both. The bar biasing member may have a loading characteristic that is substantially the same as the latch biasing member. The bar biasing member may have a loading characteristic that is greater than the latch biasing member. The bar biasing member may have a loading characteristic that is less than the latch biasing member. The one or more bar biasing members may be biased in a first direction, a second direction, or both so that a bias force of the one or more biasing members are increased. The bar biasing member and the latch biasing member may have a loading characteristic that are within about 0.005 N or more, about 0.05 N or more, or about 0.01 N or more. The bar biasing member and the latch biasing member may have a loading characteristic that are within about 5 N or less, about 3 N or less, or about 1 N or less. The one or more bar biasing members, latch biasing members, or both may exert a force of about 0.005 N or more, about 0.05 N or more, about 0.075 N or more, about 1 N or more, or about 2 N or more. The one or more bar biasing members, latch biasing members, or both may exert a force of about 30N or less, about 20 N or less, or about 10 N or less. The one or more bar biasing members, latch biasing members, or both may be in contact with a bar stop so that the bar biasing member, latch biasing members, or both is pre-loaded when the bar biasing member, the latch biasing member, or both are in the home position. The pre-load may be greater than 0 N, about 0.2 N or more, about 0.5 N or more, about 0.75 N. or more, or about 1 N or more in the home position. The pre-load may be about 30 N, or less about 20 N or less, or about 10 N or less in the home position. Preferably, the preload is about 0.5 N or more and more preferably about 0.066 N or more in the home position. A load on the bar bias member may be increased when the latch unit moves in a first direction, a second direction, or both relative to a home position of the latch unit. An increase in load or a change in load of the bar biasing member, the latch biasing member, or both may be about 1 N or more, about 3 N or more, about 5 N or more, about 7 N or more, or about 10 N or more. The increase in load or the change in load may be about 50 N or less, about 30 N or less, about 20 N or less, or about 15 N or less. The one or more bar biasing members may extend as the bar arm moves in a first direction, a second direction, away from a bar stop, or a combination thereof. The one or more bar biasing members may be compressed as the bar arm moves in a first direction, a second direction, toward a bar stop, away from a bar stop, or a combination thereof.

The one or more bar stops may function to prevent movement of the latch unit, a bar arm, a bar, or a combination thereof. The one or more bar stops may function to pre-load a bar biasing member. The one or more bar stops may be a projection from a bar frame. The one or more bar stops may be part of the bar frame that prevents longitudinal movement, rotational movement, or both of the bar arm. The one or more stops may be located on a track, in a window, or both of the bar frame. The one or more bar stops may be part of the housing, hand piece, handle, or a combination thereof. The one or more bar stops may be part of, attached to, movable with, movable relative to, or a combination thereof the latch unit, the ground member, the movable member, the movement unit, or a combination thereof. The one or more bar stops may be static. The one or more bar stops may be a molded part of the bar frame. The one or more bar stops may be located a predetermined distance from an end of the window so that the bar biasing member is biased a pre-determined amount, has a pre-load, or both. The one or more bar stops may have a similar shape and structure to a latch stop. The teachings herein for the bar stops may be used for the latch stops, or vice versa. The bar stops may be located inside of the handle, inside of the bar frame, outside of the bar frame, outside of the handle, or a combination thereof. There may be more than one bar stop. There may be an upper bar stop, a lower bar stop, or both. The one or more bar stops may restrict movement of the bar arm so that the bar arm is prevented from moving beyond a predetermined location.

The one or more bar arms may function to extend from a movable member so that a portion of the bar arm, the bar, or a combination thereof are extendable into a ground member, a latch unit, or both. The one or more bar arms may extend cantilever from the trigger, the movable member, or both. The one or more bar arms may extend partially into the latch unit, a latching pathway, around a hook latch, or a combination thereof. The one or more bar arms may be located at virtually any location on a movable member, a trigger, or both. Preferably, the one or more bar arms are located on a bottom of the movable member. The one or more bar arms may be rigid (e.g., non-flexible). The one or more bar arms may be solid and rotatable about a pivot. The one or more bar arms may be connected to the bar frame by a pivot, a pin, a bar biasing member, or a combination thereof. The one or more bar arms may be free of movement along a longitudinal axis of the movement unit, the trigger, or both. The one or more bar arms may be pivotably movable relative to the relative to the movement unit, the trigger, or both. The one or more bar arms may be elastically deformable. The one or more bar arms may be a bar biasing member. The one or more bar arms may be biased by the bar contacting a bar stop, a wall, a latching pathway, or a combination thereof. The one or more bar arms may store energy. The one or more bar arms may be pre-loaded. The one or more bar arms may be free of a pre-load. When the one or more bar arms are a bar biasing member, the one or more bar arms may have a loading characteristic when the spring is stretch, compresses, or moved from a home position (e.g., a neutral position or resting position). The loading characteristic may exert an opposing force to the one or more hook latches or the one or more hook latch biasing members. The loading characteristic of the bar arm may be substantially equal to a loading characteristic of a hook latch or hook latch biasing member. For example, when the bar and the hook latch contact each other, both the bar arm (e.g., bar biasing member) and the latch biasing member may be displaced at the same time or may be displaced in a sequence. The loading characteristic of the bar arm may be less than a loading characteristic of a hook latch or latch biasing member. For example, the latch biasing member may displace the bar arm, the bar arm may be displaced until the bar arm contacts a bar stop, or both and then latch biasing member, the hook latch, or both may be displaced. The loading characteristic of the bar arm may be greater than a loading characteristic of a hook latch or hook latch biasing member. For example, the bar arm (e.g., bar biasing member) may displace the latch biasing member, and/or the hook latch and latch biasing member may be displaced until the hook latch, the latch biasing member, or both contact a stop and the bar arm may be biased. The one or more bar arms may be linear in shape. The one or more bar arms may be tapered. The one or more bar arms may taper as the bar arms extend away from the movable member and towards the ground member. The one or more bar arms may taper in shape so that once a sufficient amount of the bar arm extends into the latch unit, the latching pathway, or both the one or more bar arms may be prevented from extending further into the latch unit, the latching pathway, or both. A distal end, narrowest region, tapered portion, end that extends into the latch unit, end that extends into the latching pathway, or a combination thereof may include one or more bars. Preferably, the one or more bars may be located on a side of the bar arm (e.g., may extend normal to the bar arm). More preferably, the one or more bars extend substantially normal from the bar arm.

The one or more bars may function to connect the movement unit to the latch unit so that movement of the movable member or movement unit relative to the ground member is prevented (e.g., create a locked state). The one or more bars may move through a pathway to connect and release a closure assembly. Preferably, the one or more bars connect a movement unit to a latch unit. More preferably, the one or more bars connect to the hook latch to form a locked state. The one or more bars may be movably mounted to move along a prescribed path. The one or more bars may be virtually any shape so that the bars are movable through a latching pathway into the latch unit and then along a pathway to create a locked state and an unlocked state. The one or more bars may contact a hook latch to create a locked state. The one or more bars may be moved away from a hook latch to move along the pathway from a locked state to an unlocked state. The one or more bars may be displaced from home position (e.g., a neutral position) in a first direction, a second direction, or both that are transverse to the prescribed path unit the one or more bars contact a bar stop that prevents movement in the first direction, the second direction, or both. When the one or more bars are biased in a first direction, the one or more hook latches may be biased in a second direction or the one or more hook latches may remain in a home position. For example, the one or more hook latches may remain in a home position by being restrained by a stop. The one or more bars may be moved and a load on the one or more bars increases above the pre-load. When the one or more hook latches are biased in a first direction, the one or more bars may be biased in a second direction or remain in a home position. For example, the one or more hook latches may remain in a home position by being restrained by a stop). Each movement unit and preferably each trigger may include only one bar, one bar arm, or both. For example, if the device includes two triggers each trigger may include a bar arm and a bar. The one or more bars may only extend along one side of the hook latch. Preferably, the one or more bars may circumnavigate the hook latch. The one or more bars may be a projection that extends from the bar arm and ultimately from a movable member or a trigger so that when the bar is trapped the movable member, the trigger, or both are prevented from being moved. The one or more bars may extend cantilever from a bar arm. The bar may be cylindrical, cubical, a cone, a cuboid, or a combination thereof. Preferably, the bar is cylindrical so that the bar may extend through a latching pathway, into the latch unit, and around a pathway of the latch unit.

The latching pathway may function to receive the bar into the latch unit, the ground member, the housing, the handpiece, the handle, or a combination thereof. The latching pathway may be an opening in the housing, hand piece, forceps, handle, or a combination thereof. The latching pathway is aligned within bar so that as the bar moves in a prescribed motion the bar will pass into and through the latching pathway. For example, the prescribed motion is the motion of the trigger about a pivot point and the bar extends into and through the latching pathway as the bar moves along this prescribed motion. The latching pathway may be an absence of material. The latching pathway may be part of the housing, handle, hand piece, or a combination thereof (e.g., a gap or spaced formed in the housing). The latching pathway may have one or more depths. The latching pathway may be an internal structure or an external structure. The latching pathway may permit the bar to extend through a portion (e.g., the bar pathway). The latching pathway may permit a portion of the bar arm to extend into the latching unit, the handle, or both (e.g., bar arm pathway). The latching pathway may have a height, width, length, or a combination thereof that permits a locking arm to extend a predetermined distance along the prescribed motion of the movable member. The latching pathway may include a bar pathway and a bar arm pathway. The bar arm pathway may be longer than the bar pathway. The bar pathway may have a thickness that is less than the bar pathway. The bar may not fit through the bar arm pathway. The bar arm pathway may contact a portion of the bar arm to restrict movement of the movable member. The bar pathway may be a deeper portion of the bar arm pathway where the bar can extend through into the latch unit. The bar arm pathway, the bar pathway, the latching pathway, or a combination thereof may allow for movement of the bar, the bar arm, or both. For example, the bar arm may longitudinally move when the bar contacts the hook latch so that a locked state is created. The latching pathway may accommodate rotational movement of the bar arm, longitudinal movement of the bar pathway, or both. The latching pathway may guide the bar, the bar arm, or both as the bar and the hook latch connect to each other, move relative to each other, form a locked state, or a combination thereof. The latching pathway may include one or more stops. The latching pathway may be a stop. The latching pathway may include a bar stop, a latch stop, or both. Preferably, the latching pathway is free of stops. The latching pathway may permit ingress and egress of the latch unit relative to the housing, the handle, hand piece, a stop, a trigger stop, an aperture, or a combination thereof. Preferably, the latching pathway is located internal of an aperture.

The one or more apertures may function to protect a latching pathway, create a stop, create a trigger stop, form an opening in an external wall of the housing, or a combination thereof. The one or more apertures may be an opening in the hand piece, housing, handle, or a combination thereof. The aperture may permit the movement unit to extend into the latch unit. The aperture may restrict movement of the movement unit relative to the latch unit. The aperture may create a trigger stop that contacts the movable member, a trigger, the cut trigger, the clamp trigger, or a combination thereof. For example, the aperture may be a trigger stop or include a trigger stop when only a predetermined amount of a trigger may extend into the aperture before the aperture contacts the trigger to restrict movement.

The trigger stop may function to restrict motion of a movable member, trigger, of both relative to a ground member, a handle, or both. The trigger stop may restrict movement of the movement unit relative to latch unit. The trigger stop may restrict movement of a trigger, a bar, or both along the prescribed path. The latching pathway may extend through the trigger stop. The trigger stop may be an outer wall of the hand piece, the handle, the housing, or a combination thereof. The trigger stop may be an inner portion of the latching pathway where the bar arm contacts so that movement is prevented. The trigger stop may be located at any location along the movable member, the ground member, or both. Preferably, the trigger stop is part of the ground member, handle, or both. The trigger stop may be flush with the trigger, the movable member, the ground member, the handle, or a combination thereof. The trigger stop may extend outward from the trigger, the movable member, the ground member, the handle, or a combination thereof. The trigger stop may be an internal wall located within the hand piece that contacts a portion of the bar arm as the bar arm travels along a prescribed motion. The trigger stop may allow the bar to contact the latch unit when the latch unit is in the lockable state and to prevent the bar from contacting all or a portion of the latch unit when the latch unit is in the unlockable state.

The latch unit may function to create a connection with a movement unit so that the movable member and the ground member are locked together. The latch unit may retain a portion of the movement unit. The latch unit and the movement unit may be movable relative to each other. The latch unit and the movement unit may be movable relative to the movement member and the ground member respectively. The latch unit may move as the movement unit moves along a prescribed path, an arcuate movement, or both (e.g., during a forward stroke, a return stroke, or both (i.e., during locking, during unlocking, or both)). For example, as the movement unit moves along the prescribed path the movement unit may move the latch unit so that the latch unit and the movement unit are moved into a locked state, an unlocked state, or both. The latch unit may move relative to the movable member, the ground member, or both. The latch unit may include a lockable state, an unlockable state, or both. The latch unit may be under a load (or pre-load) when the closure assembly is moved between or to a home position, a locked position, an unlocked position, a lockable state, an unlockable state, or a combination thereof. Preferably, the latch unit includes a pre-load when the latch unit is in the home position, the latch unit is free of contact with the movement unit, or both. The latch unit may move along a longitudinal axis (e.g., all or a portion of the latch unit may move along the handle, the hand piece or both up and down as the movement unit moves into contact with the hook latch or out of contact with the hook latch). All or a portion of the latch unit may move along a length of the handle or the ground member. The latch unit may include one part. The latch unit may include one movable part. The latch unit may include a latch bias member, latch stop, a latch plate, latch unit frame, hook latch, adjustment switch, and guide aperture. Preferably, the latch unit includes a latch plate. More preferably, the latch unit multiple pieces connected together. The latch unit may be movable relative to the movement unit when the latch unit and the movable unit are in contact. The latch unit may be constrained within the handle by a recess in the latch unit frame (e.g., a sidewall, a forward stop, a backward stop).

The latch unit frame may function to ground all or a portion of the latch unit. The latch unit frame may restrict movement of a portion of the latch unit. The latch unit frame may connect to the handle, hand piece, housing, or a combination thereof and permit movement of the latch biasing member, the latch plate, or both. The latch unit frame may include one or more walls connected together. The latch unit frame may include a plurality of walls connected together with a window therein. The window of the latch unit frame may receive a latch plate. The latch plate may be movable along the latch unit frame. The latch plate may connect to a latch biasing member directly. The latch biasing member may extend from the latch unit frame and preferably cantilevered from the latch unit frame. One or more latch stops may extend from the latch unit frame, into the window, or both. The latch unit frame may be rectangular, round, oval, square, or a combination thereof. Preferably, the latch unit frame has a major dimension (e.g., length) and a minor dimension (e.g., width). The latch plate, preferably, is movable about the major dimension of the latch unit frame. The latch unit frame may connect to one end of a latch biasing member. The latch unit frame may ground the latch biasing member so that as the latch biasing member, the latch plate, or both are displaced the latch biasing member increases in load. The latch unit frame may contact one or more sides of a latch plate, one or more ends of a latch plate, or both. For example, the latch unit frame may include a sidewall that assists in controlling movement of the latch plate laterally, longitudinally, or both. The latch unit frame may include one or more sidewalls that extend around a first side, a second side, first end, second end, or a combination thereof of the latch plate.

The sidewall may function to restrict movement of the latch unit, the latch plate, or both. The sidewall may restrict forward movement, rearward movement, downward movement, upward movement, or a combination thereof. The sidewall may extend along all or a portion of the latch unit, the latch plate, or both. The sidewall may be part of the housing, the handle, the hand piece, latch unit frame, or a combination thereof. The sidewall may restrict the latch plate so that the latch plate moves longitudinally relative to the handle. The sidewall may permit longitudinal movement but may restrict lateral movement. The sidewall may be an internal wall within the housing, the handle, the hand piece, latch unit frame, or a combination thereof. The sidewall may have an external portion and an internal portion. The sidewall may include one or more latch stops.

The one or more latch stops may function to restrict lateral movement or longitudinal movement of the latch plate relative to the latch unit frame. The latch stop may be located between a latch movement unit and an end of the latch unit frame. The latch stop may prevent the bar movement unit from moving towards an end. The latch stop may prevent full extension, full contraction, or both of the latch biasing member. The latch stop may be an internal wall of the ground member, the latch unit, or both. The one or more latch stops may be part of, attached to, movable with, movable relative to, or a combination thereof the latch unit, the ground member, the movable member, the movement unit, or a combination thereof. The one or more latch stops may maintain the one or more latch biasing members with a pre-load when the one or more hook latches are in a home position. The latch stop may be a wall that moves with the bar unit to restrict movement of the bar relative to the hook latch. The latch stop may be a static piece. The latch stop may be located above (e.g., in a plane over the return apex when the return apex is located above the entry apex) the bar, the hook latch, or both. The latch stop may be located below (e.g., in a plane under the entry apex when the entry apex is located below the return apex) the bar, the hook latch, or both. The latch stop may be connected to the bar stop. The latch stop and bar stop may be located on a same wall, in a same plane, in a different plane, in a stepped manner, or a combination thereof. There may be one or more latch stops. There may be a plurality of latch stops. There may be a first latch stop on a first side (e.g., above or below) and a second latch stop on a second side (e.g., above or below) that opposes the first latch stop. A first latch stop and a second latch stop may be on a same side and in a different plane. The latch stops may be part of the latch unit frame. The latch stops, latch unit frame, or both may be covered by a selection plate.

The selection plate may function to change the closure assembly between a lockable state and an unlockable state. The selection plate may move along a sliding axis, a switch path, or both to activate and deactivate the closure assembly (e.g., change the latch unit between a lockable state and an unlockable state). The selection plate may include an adjustment switch that extends out of the housing, hand piece, handle, or a combination thereof an is exposed for movement by the user.

The adjustment switch may function to move the closure assembly, deactivate the closure assembly, activate the closure assembly, or a combination thereof. The adjustment switch may be exposed so that upon a force being applied to the adjustment switch the state of the closure assembly is changed. The adjustment switch may be movable along a switch path. The adjustment switch may move the selection plate so that the latch plate is moved between the unlockable state and the lockable state to change the function of the closure assembly (e.g., activate and deactivate).

The unlockable state detent and lockable state detents function to allow free movement of the movable member and the ground member relative to each other by locking the position of the latch unit out of the path of the movement unit or a distance from the movement unit so that the movement unit cannot lock to the ground unit or permit locking of the movable member relative to the ground member respectively. The unlockable state detent and the lockable state detent (hereinafter detents) may lock the selection plate, the latch plate, or both in a lockable state or an unlockable state. The detents may allow a user to select if the closure assembly is activated or deactivated. The detents may be one or more recesses that selectively receive a detent pin to select the state of the closure assembly.

The detent pin functions to create a locked state, an unlocked state, or both with the closure assembly. The detent pin functions to contact a detent and then lock the latch plate in a selected location. The one or more detent pins may be a projection that contacts a detent to retain selection of a desired state. The one or more detent pins, detents, or both may be part of the one or more latch plates.

The one or more latch plates may function to move when a hook latch is contacted by a bar so that a locked state, an unlocked state, or both are created. The latch plate may carry one or more elements that form the pathway (e.g., a path that a bar moves along as the bar moves from a locked state to an unlocked state). The latch plate may carry or include the bias member, detent pin, one or more detents, the hook latch, the wall guide, guide aperture, connection pin, selection plate, adjustment switch, or a combination thereof. The latch plate may be free of a detent pin, detent, wall guide, guide aperture, selection plate, adjustment switch, or a combination thereof. Preferably, the latch plate is an integral piece that includes the bias member having a detent pin and an adjustment switch, a selection plate including a hook latch, wall guide, and guide aperture. The latch plate may be a latch biasing member. The latch plate may rest in a home state and then move once acted upon by the movement unit and preferably a bar. The latch plate may only move or be movable when the latch unit is in a lockable state (e.g., during locking or unlocking of the closure assembly or moving the closure assembly between a lockable state and an unlockable state). The latch plate may only move when displaced by the movement unit. The latch plate may move along the prescribed motion between the lockable state and the unlockable state. All or a portion of the latch plate may move in the direction of the prescribed motion, along the prescribed motion, or both between a first state (e.g., lockable state) and a second state (e.g., unlockable state). The latch plate may include one or more detents, a detent pin, or both that assist in locking the latch plate in each state (e.g., the unlockable state, the lockable state, or both). The latch plate may move along the sliding axis, tracks, the hand piece, the housing, or a combination thereof. The latch plate may rotate about an axis. The latch plate may be flexible so that the hook latch is movable from the home position. The latch plate may carry the hook latch and return the hook latch to a home position. The latch plate may move in a longitudinal direction, along a longitudinal axis, or both of the hand piece, the handle, the latch plate, or a combination thereof (e.g., the latch plate path). The latch plate path may be a longitudinal movement of the latch plate up and down, toward and away from the home position, or both. Preferably, the latch plate path extends along the prescribed motion of the bar. The latch plate path may move along or transverse to a prescribed path of the bar. The latch plate may move away from an into contact with a latch stop. The latch plate and the latch stop may be in contact when the latch unit is in the home position. The latch plate may longitudinally move as a bias member expands, contracts, or both. The one or more latch plates may be connected to, in contact with, or both a bias member and preferably a latch bias member. The one or more latch plates may be a latch bias member.

The bias members (e.g., bar biasing member, latch biasing member, or both (herein after bias member)) may function to store energy when a force is applied to the latch plate or the bar (or bar arm) and then to release the energy when the force is removed. The bias member may function to move the latch plate or bar to a home position. The bias member may assist in locking or unlocking the movable member and the ground member. The bias member may be any material that may store energy. The bias member may be a double acting member. For example, a load of the bias member may be increased in a first direction and increased in a second direction. The home position may be a zero load state or zero energy state. The first direction and the second direction may be relative to the home position. The biasing member may act upon the housing, the hook latch, latch unit frame, or a combination thereof. The biasing member may act upon the housing, bar, bar frame, or a combination thereof. The bias member may be a dual acting member that acts on two members simultaneously. The bias member may be free of a load when the bias member is in a home position. The bias member may have a pre-load when the bar bias member is in the home position. The bias member may be elastomeric, rubber, a spring steel, helical, round, cylindrical, a torsion spring, a cantilevered spring steel, or a combination thereof. The bias member may be a piece of rubber that is compressible, expandable, or both. Preferably, the bias member is a dual acting bias member. More preferably, the bias member is a deformable body that includes a plurality of elastically deformable connections. The plurality of elastically deformable connections may be connected to each other, movable relative to each other, or both to store and release energy. The bias member, the plurality of elastically deformable connections, or both may be elastically deformable. The biasing member may provide a bias between the hook latch and the housing or a bar latch unit and the housing. The bias member when expanded, contracted, or both may have a load. The bias member may increase in load as the bias member moves away from latch plate moves away from the home position. A load on the bias member may be increased when the latch unit moves in a first direction, a second direction, or both relative to a home position of the latch unit. The change in load on the bias member may exponentially increase as a distance of the latch unit form a home position increases. The change in load may be sufficiently large so that the bias member returns the latch unit back to the home position when the latch unit moves from a locked state to an unlocked state, in an unlockable state, a lockable state when the hook latch is not biased, or a combination thereof. The bias member may be a double acting bias member. The bias member may bias towards the home position regardless of whether the bias member is biased in a first direction or a second direction. The bias member may be compressed, expanded, or both when the hook latch and bar contact each other and the bar and the hook latch move relative to each other.

The hook latch may function to create the locked state. The hook latch may function to catch the bar and prevent movement of the movable member relative to the ground member. The hook latch may selectively receive one or more bars. The one or more hook latches may be displaced from a latch neutral position in a first direction, a second direction, or both that is transverse to the prescribed path. The hook latch and the bar may be in contact a first time, a second time, or both. The hook latch may have two sides or more, three sides or more, or four sides or more. The hook latch may have a first side that assists in creating a locked state. The hook latch may have a second side that assist in retaining a bar so that the locked state is maintained. The hook latch may have a third side that assists in creating an unlocked state. The hook latch may be generally triangular in shape or may have a portion that is triangular in shape. The hook latch when contacted may longitudinally move the latch plate or a latch biasing member. The hook latch when contacted may move in a first direction that expands or contracts the bias member from a home state so that a load is applied to the bias member, energy is stored in the bias member, or both. The hook latch when contacted may move in a second direction that expands or contracts the bias member from a home state so that a load is applied to the bias member, energy is stored in the bias member, or both. Preferably, the hook latch when moved in a first direction will expand the bias member and when moved in a second direction will compress the bias member. The hook latch may include an angled portion, a linear portion, an entry apex, an entry portion, a return portion, an exit apex, pocket, or a combination thereof.

The one or more entry portions may function to assist in creating a locked state when the bar contacts the one or more entry portions. The one or more entry portions may guide a bar to an entry apex, the pocket, or both. All or a portion of the one or more entry portions may be aligned with the latching pathway when the selection plate is in the lockable state. The one or more entry portions may be an angled portion that may be angled so that all or a portion of the one or more angled portion extends across an opening of the latching pathway. The entry portion may extend perpendicular to a longitudinal axis of the handle, the latch plate, or both. Preferably, the entry portion extends at an angle of about 90 degrees or less, about 75 degrees or less, about 60 degrees or less, about 45 degrees or less, or about 30 degrees or more relative to the longitudinal axis of the handle, the latch plate, or both. The one or more entry portions may extend in or transverse to the path of the prescribed motion (e.g., prescribed path) of the bar so that the bar contacts the entry portion. The entry portion may be angled so that as the bar extends along the prescribed motion the bar is moved towards the entry apex and ultimately the pocket. The entry portion may have a sufficiently small angle so that as the bar moves along the entry portion the latch plate is moved, compressing or extending the bias member, by a force being exerted upon the entry portion of the hook latch. The latch plate or hook latch may continue to move as the bar travels along the entry portion until the bar reaches the entry apex. The entry portion may terminate at an entry apex.

The entry apex may function to assist the bar in entering the pocket, leaving the entry portion, or both. The entry apex may be a part of the hook latch. The entry apex may prevent the bar from exiting the pocket from a same direction the bar entered the pocket. The entry apex may be where two walls converge together. The entry apex may be where the entry portion and the curved portion converge. The entry apex may be a point where a bar may be required to be on a first side or a second side of the hook latch. The entry apex may create a lip at the pocket so that the bar cannot be back driven. When the bar passes the entry apex the bias member may release some or all of its stored energy so that the bar is moved into the pocket. When the hook latch, the latch plate, or both are in the lockable state the bar may extend around the entry apex into the pocket. The entry apex and an exit apex may be located on opposing sides of the pocket, the curved wall, or both.

The pocket may function to receive the bar so that a locked state is formed. The pocket functions to restrict movement of the bar. The pocket may be a wall that the bar is biased against so that the bar is restricted from being moved back into the latching pathway. The pocket may be a curved portion of the hook latch. The pocket may be a recess that the bar resides within so that the locked state is formed and the bar is not inadvertently moved out of the pocket. The pocket may resist a biasing force of the movable member away from the ground member. For example, the movable member may be biased away from the ground member and the pocket may resist the bar from exiting the pocket. In another example, the trigger may be biased apart from the hand piece by a bias device and the bias device may assist in moving the bar into the pocket. The pocket may resist a bias force in a lateral direction, a longitudinal direction, or both. The pocket may resist the biasing member from moving to the home position. The pocket may prevent longitudinal movement, lateral movement, or both of the bar. The exit apex, the entry apex, or both may extend beyond the pocket so that the bar remains within the pocket until a bias force of the movable member is resisted, a user regrips the movable member and the ground member together, or both. Upon regripping, resisting a bias force, or both the bar may exit the pocket by extending around the exit apex.

The exit apex may function to prevent a bar from inadvertently exiting the pocket, the curved portion, or both. The exit apex may extend beyond the pocket. The exit apex may be where the return portion and the curved portion converge. The exit apex may be a point that once the bar extends beyond the bar cannot reenter the pocket. The bar may contact the exit apex while exiting so that the latch plate is biased, the latch biasing member is biased or unbiased, and upon the bar stopping contact with the exit apex, the latch plate (or bar biasing member) may bias away from the bar, to the home position, or both so that the prescribed motion of the bar is above the pocket and the bar cannot reenter the pocket. The exit apex may be formed between the pocket and the return portion.

The return portion may function to guide the bar from the locked state to an unlocked state. The return portion may function to guide the bar to the latching pathway. The return portion may be located below the prescribed path when the latch plate is in the home position. Preferably, the return portion is located below an upper portion of the pathway when the hook latch is in the home position. The return portion may be a linear portion. The return portion may be located above the latching pathway when the latch plate is in the home position. For example, the hook latch may block the latching pathway when the latch plate is in the home position, and as the bar moves along a prescribed path the bar may contact the return portion of the hook latch and move the hook latch (e.g., down) to open the latching pathway. For example, the bar may push the hook latch down by contacting the return portion so that the release apex is located below the latching pathway and the bar can exit the handle, the hand piece, the latch unit, housing, or a combination thereof. As the latching pathway is being opened the bias device may be compresses and store energy within the bias device. Once the bar stops contacting the return portion (e.g., leaves the pathway) and reenters the latching pathway the bias device may bias the latch plate back to a home position. The return portion may be moved into alignment with the latching pathway when the bar moves along the pathway towards the latching pathway.

The pathway may function to guide the bar from a home position to a locked position, from a locked position to an unlocked position, from an unlocked position to a home position, or a combination thereof. The pathway may align with the latching pathway, the bar pathway, the bar arm pathway, or a combination thereof. The pathway may be out of alignment with the latching pathway. The pathway may assist a bar in circumnavigating a hook latch, the pathway may extend around the hook latch, or both. The pathway may be tortuous. The pathway may be a labyrinth. The pathway may be an open area in the movement unit that the bar is guided through. The pathway may be an area between two or more walls that a bar moves through, a bar moves along, or both. The pathway may be linear or have linear portions. The pathway may have curved portions, arcuate portions, straight portions, extend 360 degrees, have serpentine portions, or a combination thereof. The pathway may begin and end at a latching pathway. The pathway may extend along an entry portion, along a return portion, around an entry apex, into a pocket, around an exit apex, around a guide apex, around a release apex, along a rear wall, or a combination thereof. The pathway may assist the bar in moving along one or more walls of the hook latch. The pathway may assist the bar in moving the latch plate as the bar and the hook latch contact each other. The pathway may be out of alignment with the hook latch, the wall guide, or both when the latch unit is in the unlocked position, the unlocked state, the unlockable state, or a combination thereof. The pathway may guide the bar around the entry apex, the exit apex, the release apex, or all of the apexes.

The release apex may function to guide the bar into the pathway and out of the pathway. The release apex may align an entry end of the pathway with the latching pathway when the latch unit is in the lockable state, unlocked state, or both. The release apex may align an exit end of the pathway with the latching pathway when the latch unit is in the lockable state, unlocked state, or both. The release apex may move from a first side of a latching pathway to a second side of a latching pathway. The release apex may be located in an upper half of the latching pathway when the hook latch is in the home state. The release apex may connect the pathway to the latching pathway. The release apex may form a point of the hook latch. The release apex may be a beginning and end of the hook latch. The release apex may be located opposite the pocket. The release apex may direct a bar to a predetermined location depending on the location of the bar relative to the release apex. For example, if the bar is located in the latching pathway the release apex may direct the bar to the entry portion and if the bar is located in the pathway the release apex may direct the bar to the latching pathway. The release apex may interfere with the arcuate movement of the bar so that the bar is directed into contact with a desired part of the hook latch.

The arcuate movement may function to move the bar from a home position, to a locked position, to an unlocked position, or a combination thereof. The arcuate movement may be an arcuate locking path, an arcuate release path, an arcuate trigger path, or a combination thereof. The arcuate movement may travel a same path in a forward direction (i.e., forward stroke) as a backward direction (i.e., return stroke). The arcuate movement may be a movement of the bar, the trigger, a movable member, or a combination thereof as the bar, the trigger, a movable member, or a combination thereof rotate about a pivot. The arcuate movement may be a prescribed movement of the bar, the trigger, the movable member, or a combination thereof about a pivot. The arcuate movement may be the only movement the trigger, the bar, the movable member, or a combination thereof makes. The arcuate movement may move the bar from a home position to a locked position, a locked position to an unlocked position, and an unlocked position back to a home position.

The home position may be a position where the latch plate is at steady state, the bar is not within the latch unit, the bar is at a neutral position, the hook latch is a neutral position, the bias members are at a zero state, the bias members are resting against a stop with a pre-load. The home position may be a position where the bias member is free of compression. The latch plate may move from a locked position to a home position or vice versa, an unlocked position to a home position or vice versa, or both. The home position may be where the hook latch crosses the latching pathway. The home position may be where the bias member returns the latch plate upon an engagement force or a disengagement force being removed. The home position may be a bar neutral position, a latch neutral position, or both. The home position may be where the movement unit and the latch unit are disconnected, can move relative to each other, or both. The bar may move from an unlocked position to a home position and be free of a home position. The bar may move from a locked position to an unlocked position and then to a home position. Preferably, the bar, movable member, ground member, hook latch, latch unit, bar unit, or a combination thereof are at a home position when the device is in an unlocked state. When the bar contacts the hook latch, a contact position may be created.

The contact position may be any position when the part and hook latch are in contact when the bar is not located within the pocket. The contact position may be an unlocked position where the bar is moving towards or away from a locked position. The locked position may be where the bar is located within the pocket and the bar is prevented from moving by the hook latch. The locked position may be where the bar is located between the entry apex and the exit apex. The locked position may be where the movable member moves the bar back towards the hook latch so that the bar is retained in the pocket and the movable member is prevented from moving. The locked position may be the position where the bar prevents the movable member, a trigger, or both from moving. The locked position may be where the hook latch is aligned with the latching pathway. In the locked position, the bar may bias the hook latch up or in a first direction (i.e., towards a top) as the bar enters the pathway. In the locked position, the bar may bias the hook latch down or in a second direction, which is opposite the first direction as the bar exits the pathway. In the locked position, the hook latch may be moved by the bar as the bar moves along the arcuate movement, the pathway, or both. The latch plate may be locked by the locked state detent when the latch unit is in the locked position. The locked position may be located between two contact positions or two unlocked positions.

The unlocked position may function to allow the bar to move within the pathway. The unlocked position may be any position where the bar is within the pathway but not located within the pocket. The unlocked position may be a bar in the pathway moving along the entry portion, the return portion, or both. The unlocked position may be where the bar is not located between the entry apex and the exit apex. The unlocked position may be the contact position. The bar may make a locking movement so that the bar changes from an unlocked position to a locked position.

The locking movement may be where the bar extends from an unlocked position to a locked position. The locking movement may be where the bar extends around an entry apex. The locking movement may be where the bar moves into contact with the guide apex and then upon release of the trigger, the movable member, or both the bar is moved into the pocket, from the guide apex into the pocket, into contact with the exit apex but is retained in the pocket, or a combination thereof. The locking movement may be where the bar enters the pocket. The locking movement may generate bias in both the bar and the hook latch. The latch bias member, the bar bias member, or both may be biased during a locking movement so that once the bar extends around an entry apex both the bar bias member and the latch bias member release some or all of their respective energy cause the bar to lock with the hook latch. As the bar makes a locking movement the bar may bias the bias member so that the bias member has a load. Once the bar completes the locking movement and moves into the pocket the bias member may retain some bias. The locking movement may be followed by an unlocking movement where the bar is released from the pocket.

The unlocking movement may function to release the bar from the pocket. The unlocking movement may be a movement around the exit apex. The unlocking movement may be a movement from the pocket around the exit apex, to a location above the exit apex, or both. The unlocking movement may extend away from the hook latch and then back towards the hook latch once the bar is above the exit apex or once the hook latch deflects out of alignment with the bar. Once the bar extends around the exit apex the hook latch or the bar may move back to a home position. The unlocking movement may result in the bar being in an unlocked state. An unlocking movement may move the selection plate between a lockable state and an unlockable state. The unlocking movement may be followed by a resetting movement (e.g., a portion of a return stroke) where the bar is moved back to a starting position, the bar moves out of the latch unit, the trigger and handle move back to a home position, or a combination thereof. The resetting movement may function to reset the bar. The resetting movement may be a movement around the release apex, through the latching pathway, or both. The resetting movement may result in the bar being in an unlocked state. The resetting movement may be a movement along the return portion of the hook latch, through the latching pathway, or both. The resetting movement may be the bar moving along a portion of an arcuate release path. The resetting movement may bias the latch plate in a second direction so that the bar aligns with the latching pathway, can extend around the release apex, or both. The resetting movement may be a movement of the bar towards the latching pathway regardless of if the latch unit is in the lockable state, the unlockable state, or both.

The unlockable state may function to prevent the closure assembly from being locked. The unlockable state may be where the latch state is moved to a second position where the latch unit and the movement unit are not aligned, a distance is too great for the bar to travel to the pocket, or both. The latch plate may be moved from the unlockable state to the lockable state by a user to control movement of the movable member, the trigger, or both.

The lockable state may function to allow the closure assembly to be latched. The lockable state may be a state where the movement unit and the latch unit are aligned and may connect together, may lock a movable member to a ground member, or both. The closure assembly, in the lockable state may have an unlocked state or a locked state. The unlocked state may be where the movable member and the ground member are movable relative to each other. The unlocked state may be where the bar is not constrained by the latch unit. The unlocked state may be where the latch unit is in a lockable state but the bar is not located within the pocket so that the bar is movable relative to the hook latch. The bar in the unlocked state may be in contact with any part of the hook latch except for the pocket. The latch unit may in a lockable state and changed between a locked state and an unlocked state, the bar may be movable between a locked state and an unlocked state, or both.

The locked state may function to lock the movable member and the ground member together. The locked state may be where the bar is located within a pocket. The locked state may be where the latch plate is restricted from moving about a sliding axis by the bar.

The sliding axis may function to move the latch plate from a first position to second position, along the track, up and down, parallel to a length of the handle, or a combination thereof. As the latch plate moves along the sliding axis compression of the bias member may be increased, decreased, or a combination of both. The sliding axis may be a direction of rotation of the bar, the hook latch, or both when the bar and the hook latch contact each other and rotate. The as the bar moves along the hook latch, an engaging force may be applied to the hook latch that moves the latch plate along the sliding axis.

The engaging force (e.g., a force applied during a forward stroke) may function to move the latch plate along the sliding axis, to compress the bias member, to lock the closure assembly, to lock the movement unit to the latch unit, or a combination thereof. The engaging force may be sufficiently large to move the latch plate as the two bias member compresses or stretch (e.g., a bar biasing member and a latch biasing member). The engaging force may increase as the bar moves along the hook latch. The engaging force may increase as the bar moves from the release apex towards the entry apex. The engaging force may increase as the bar moves along the return portion. The engaging force may increase as the bar moves from the exit apex to the release apex. Preferably, the engaging force is along a first side of the hook latch, along the entry portion, or both as the bar extends from the latching pathway and into the pocket. The engaging force may be a single force that is generated by a user as the bar moves along a prescribed movement an arcuate movement, or both. The user may generate the engaging force by moving the movable member and the ground member towards each other. The engaging force may be substantially similar to an amount of force required for a disengaging force.

The disengaging force (e.g., a force applied during a return stroke) may function to move the bar out of the pocket, around the exit apex, or both. The disengaging force may be a single bias member. The disengaging force may be a combination of two biasing members. The disengaging force may be created by the bar biasing member, the latch biasing member, the trigger bias member. The disengaging force may extend parallel to or along a same line as the engaging force. The disengaging force may have one or more forces along one or more different directions, vectors, or both. The disengaging force may remove a bar from the pocket and then remove the bar from the latch unit, the housing, the handle, the hand piece, or a combination thereof. The disengaging force may have a portion that is along the exit apex, along the return portion, or both. The disengaging force may be generated by a movable member bias member after the movable member is reengaged and the movable member is moved relative to the ground member. The disengaging force may first extend away from the hook latch, then up the rear wall, around the exit apex, and then along the return portion where the latch plate is moved along the sliding axis. The disengaging force may have a first disengaging force where the bar is moved out of the pocket and a second disengaging force where the bar is aligned with the latching pathway. The first disengaging force may move the bar away from the pocket (i.e., a regrip of the movable member or the trigger), up over the exit apex, or both. The first disengaging force may release the closure assembly, move the closure assembly from a locked state to an unlocked state, or both. Once the bar, movement unit, or both are released the bar, movement unit, or both may change from a first disengagement force to a second disengagement force. The second disengagement force may move the latch plate along the sliding axis so that the bar is aligned with the latching pathway. The second disengagement force may be sufficiently large to compress the bias member. The second disengagement force may increase as the bar moves along the prescribed motion, the arcuate movement or both. The second disengagement force may move the latch plate from a home position to an unlocked position where the bar may separate from the latch unit. The disengaging force may be a force generated to move the movable member from a locked state to an unlocked state and the disengaging force may be started by a user creating the force in a first direction and then a bias member may create a second disengaging force in a second opposing direction. As a disengaging force is being applied (either in the first direction or the second direction) the bar, the hook latch, or both may bias the bar, the hook, or both transverse to a direction of the disengaging force, the arcuate movement or both.

FIG. 1 illustrates a top perspective view of an electrosurgical device 2. The electrosurgical device 2 is shown as forceps 10 including a handpiece 4 that is attached to a first working arm 20 having a first jaw 16 and a second working arm 22 having a second jaw 18, and with a blade 27 located between the first working arm 20 and the second working arm 22. The handpiece 4 includes a closure assembly 28 that is connected to the movable member 12 and the adjacent member 14, which as shown are the first working arm 20 and the second working arm 22. The closure assembly 28 assists in maintaining the first working arm 20 and the second working arm 22 in a closed state when the closure assembly 28 is activated.

Figure 2:
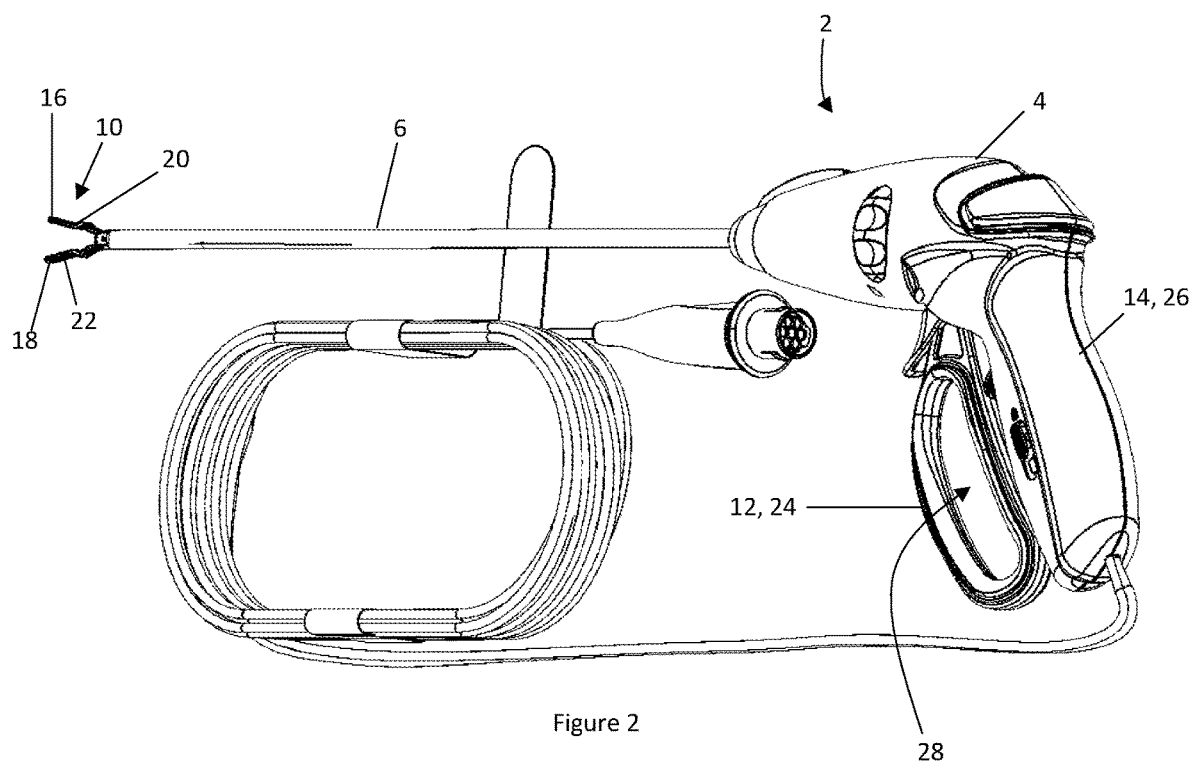
FIG. 2 is a perspective view of an electrosurgical device having a latching assembly.

FIG. 2 is a rear perspective view of the electrosurgical device 2 including the handpiece 4, forceps 10, and a stylet 6. The forceps 10 include a first working arm 20 with a first jaw 16 and a second working arm 22 with a second jaw 18. The handpiece 4 includes the closure assembly 28 that prevents movement of the first working arm 20 and the second working arm 22 by locking the movable member 12 and the adjacent member 14 in a position. The movable member 12 is a trigger 24 and the adjacent member 14 is a handle 26.

Figure 3:
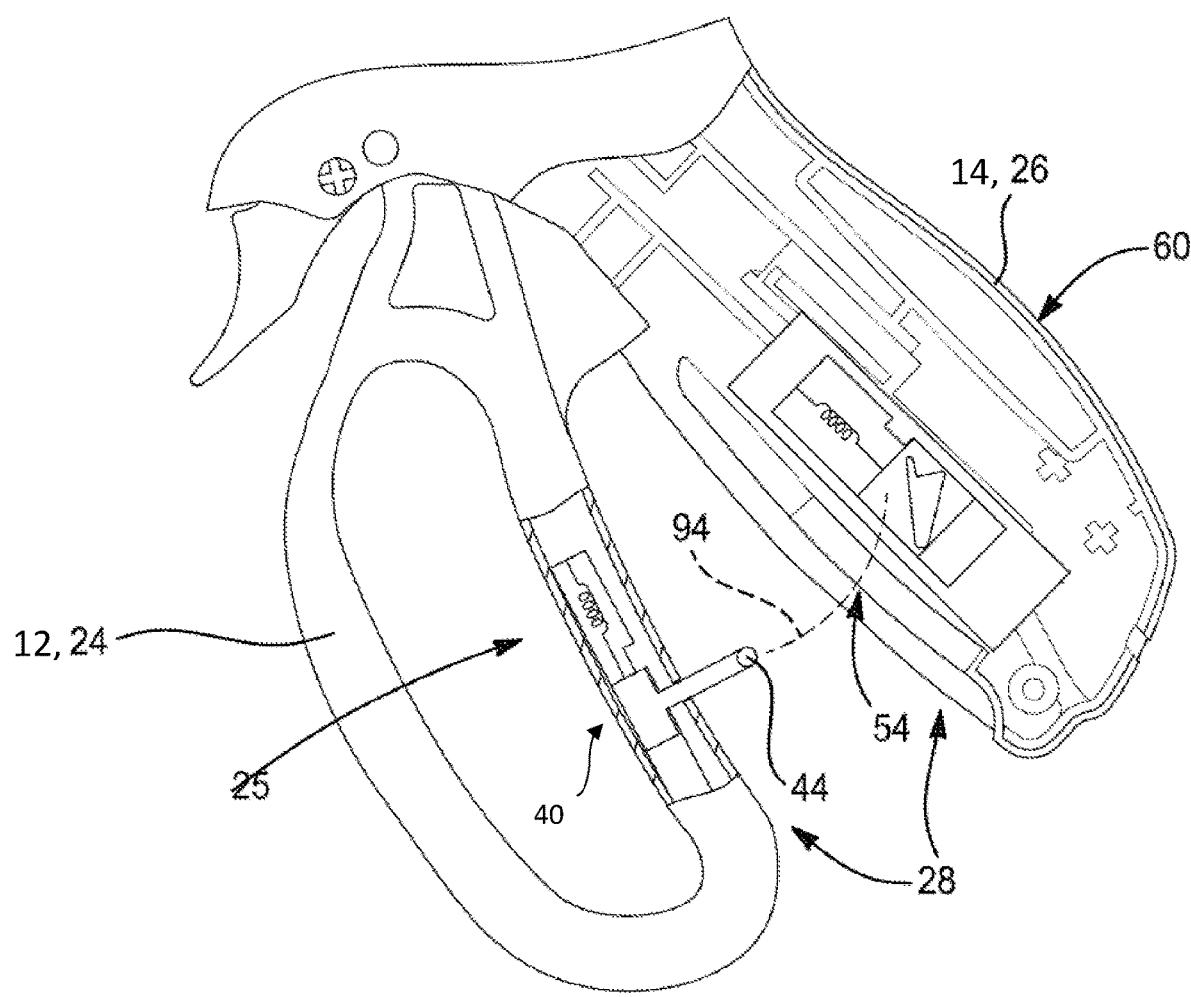
FIG. 3 is a close-up view of a movement unit and a latch unit in a lockable state.

FIG. 3 is a cross-sectional view of a closure assembly 28 including a movement unit 25 and a latch unit 60. The movement unit 25 includes the trigger 24 and a bar unit 40. The latch unit 60 is located the handle 26. As the movable member 12 moves towards the adjacent member 14 the bar 44 of the movement unit 25 has an arcuate movement 94 and extends through the latching pathway 54 into the handle 26 and in contact with the latch unit 60.

Figure 4:
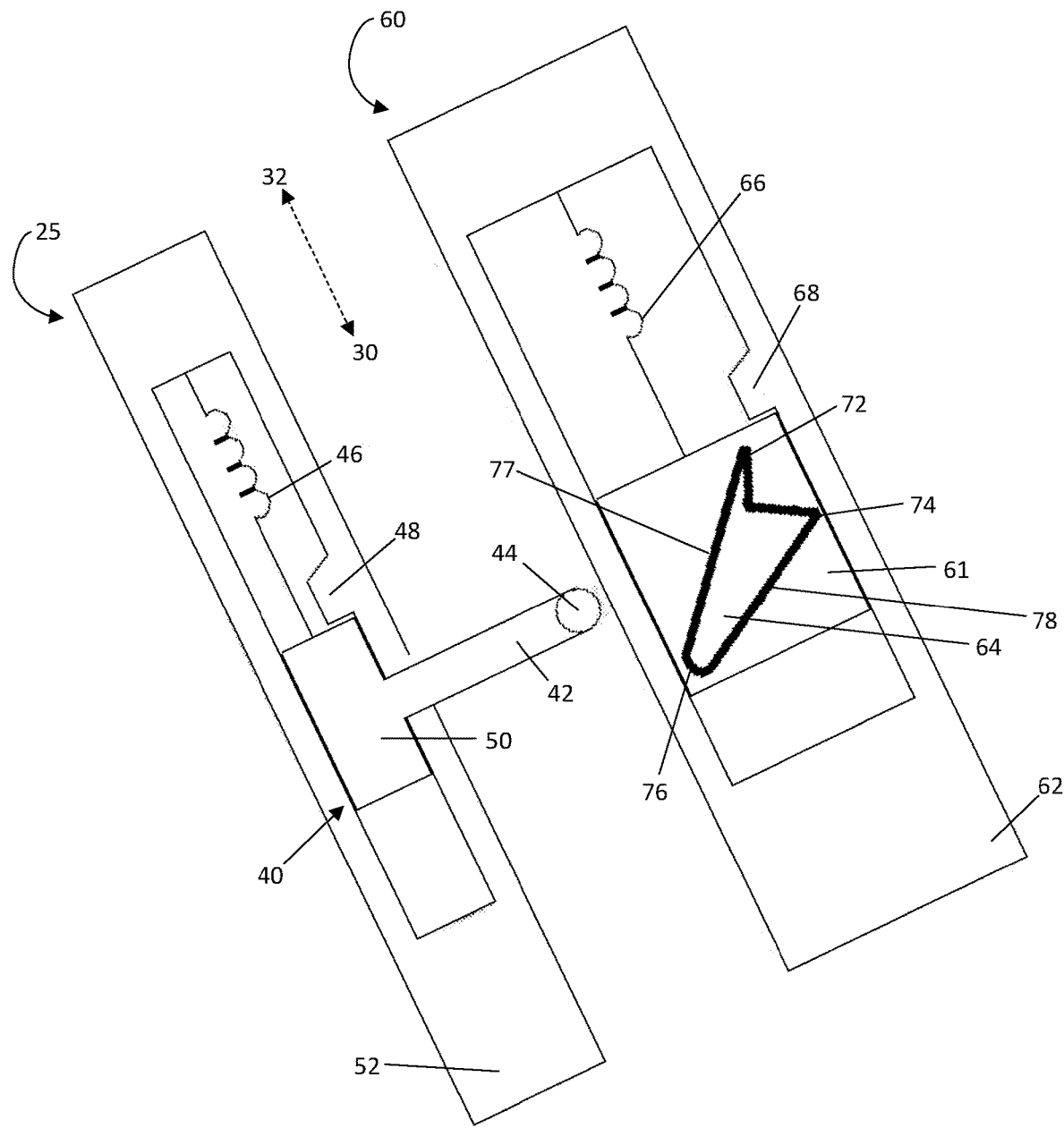
FIG. 4 is a close-up view of a movement unit and a latch unit.

FIG. 4 is a close-up view of the movement unit 25 and the latch unit 60. The movement unit 25 includes a bar unit 40 that is movable along a bar frame 52. The bar unit 40 includes a bar movement unit 50 that moves in either a direction of positive bias 30 or a direction of negative bias 32. A bar biasing member 46 connects the bar movement unit 50 to the bar frame 52. The bar biasing member 46 exerts a constant load on the bar movement unit 50 in the direction of negative bias 32. The load effectuated by the bar biasing member 46 causes the bar movement unit 50 to rest on a bar stop 48 where a pre-load is always applied to the bar unit 40. A bar arm 42 having a bar 44 at an end of the bar arm 42 are connected to and extend from the bar movement unit 50. The latch unit 60 includes a latch unit frame 62 within which a latch movement unit 61 moves in the direction of positive bias 30 or the direction of negative bias 32. A latch biasing member 66 connects the latch movement unit 61 to the latch unit frame 62 and biases the latch movement unit 61 relative to the latch unit frame 62. The latch biasing member 66 exerts a constant load on the latch movement unit 61 the direction of negative bias 32. The latch movement unit 61 is biased by the latch biasing member 66 so that the latch movement unit 61 rests on a latch stop 68. The latch movement unit 61 includes a hook latch 64, which includes an entry apex 72, an exit apex 74, a release apex 76, an entry portion 77, and a return portion 78.

FIGS. 5A-5H are close-up views of the movement unit 25 and the latch unit 60 of the closure assembly 28, in a series displaying the locking and unlocking action of the movement unit 25 and the latch unit 60.

Figure 5A:
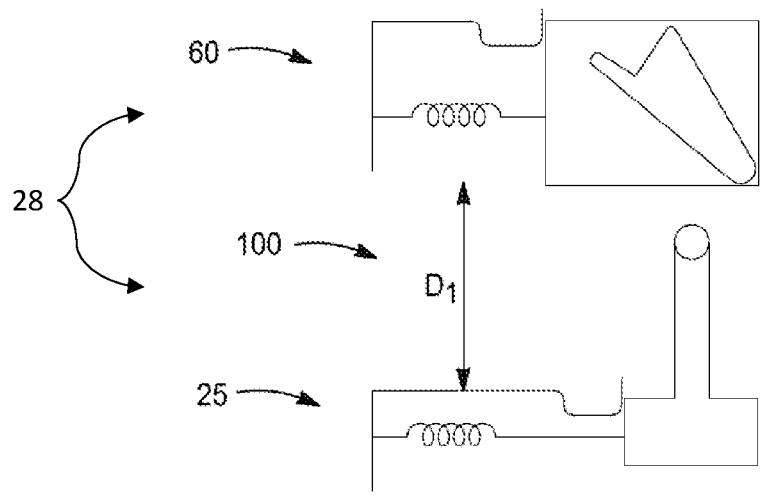
FIG. 5A illustrates the movement unit and the latch unit in the home position.

In FIG. 5A the movement unit 25 and the latch unit 60 of the closure assembly 28 are in a home position 100. At the home position 100, the movement unit 25 and the latch unit 60 are a distance $D_1$ from each other.

Figure 5B:
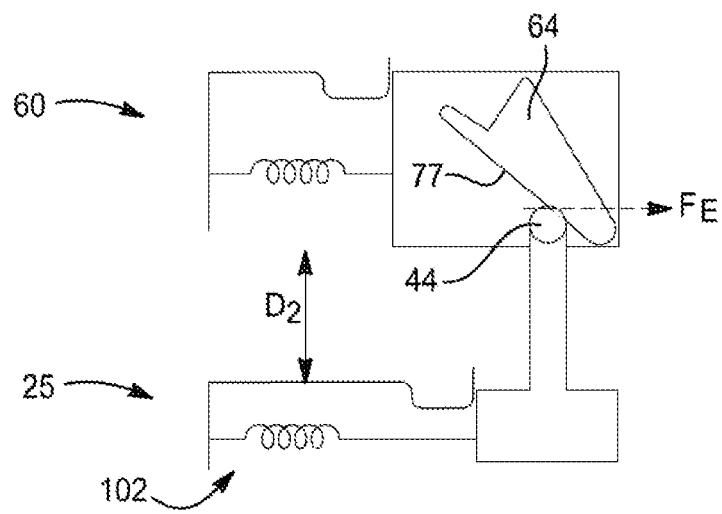
FIG. 5B illustrates the movement unit and the latch unit in a contact position.

In FIG. 5B the movement unit 25 and the latch unit 60 are in a contact position 102. In the contact position 102, the gap between the movement unit 25 and the latch unit 60 is reduced to a distance $D_2$ and the bar 44 contacts the entry portion 77 of the hook latch 64 and exerts an entry force $F_E$ on the hook latch 64.

Figure 5C:
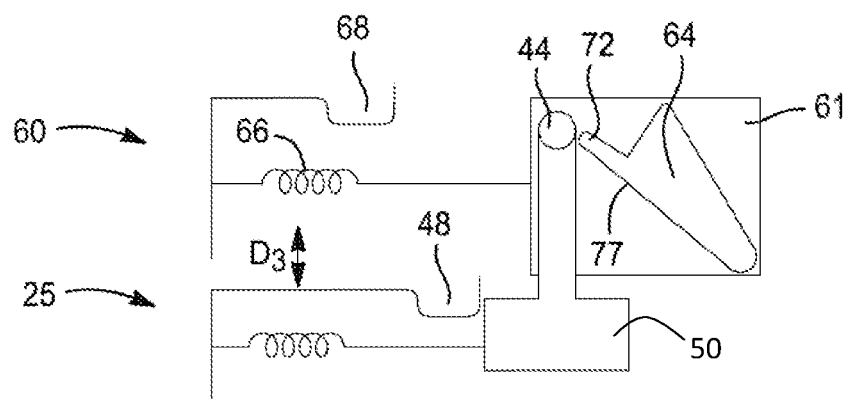
FIG. 5C illustrates the latch unit separated from a latch stop with a bar being at an entry apex.

In FIG. 5C the gap between the movement unit 25 and the latch unit 60 reduces to a distance $D_3$ causing the bar 44 to move along the entry portion 77 and positively bias the hook latch 64. The bias on the hook latch 64 displaces the hook latch 64 away from the latch stop 68 as the bar 44 slides along the entry portion 77 toward the entry apex 72. Contact between the bar 44 and the hook latch 64 causes movement of the latch movement unit 61 away from the latch stop 68 forming a gap therebetween and increasing an amount of bias created by the latch biasing member 66. The bar movement unit 50 remains biased against the bar stop 48 as the latch movement unit 61 is biased away from the latch stop 68.

Figure 5D:
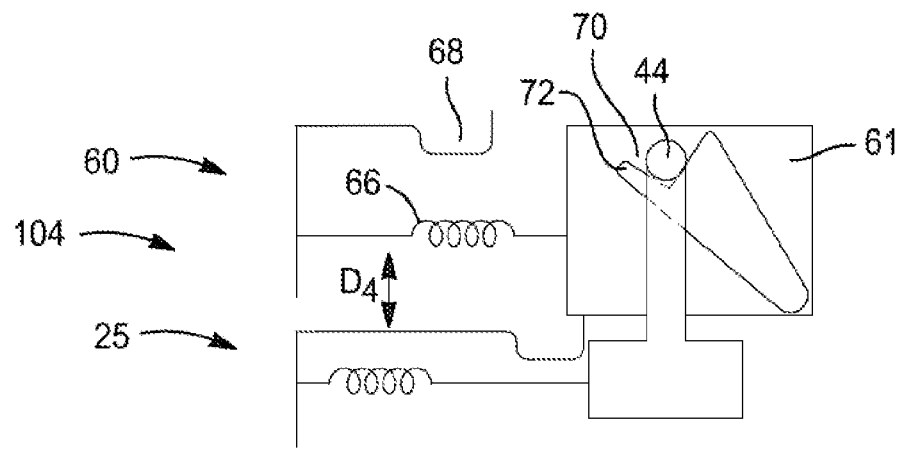
FIG. 5D illustrates the latch unit and the movement unit in a locked position with the bar being located in a pocket.

In FIG. 5D the movement unit 25 and the latch unit 60 are in a latched position 104. As the bar 44 of the movement unit 25 moves past the entry apex 72, the stored energy in the latch biasing member 66 is released so that the latch movement unit 61 is biased toward the latch stop 68 and the bar 44 falls toward the pocket 70. The latch movement unit 61 is prevented from moving back to contacting the latch stop 68 as a result of the bar 44 fitting within the pocket 70. An increase in the gap between the movement unit 25 and the latch unit 60 to a distance D4 results in the bar 44 coming to rest in the pocket 70.

Figure 5E:
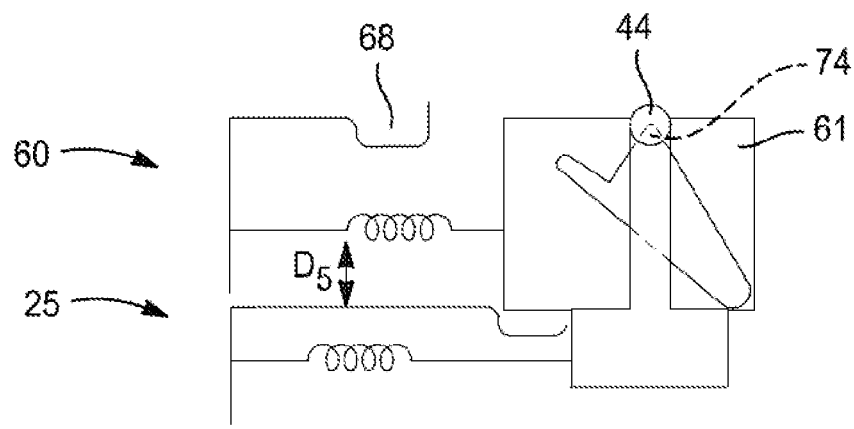
FIG. 5E illustrates the bar located at the exit apex leaving the pocket.

In FIG. 5E, the gap between the movement unit 25 and the latch unit 60 is decreased to a distance $D_5$ which moves the bar 44 past an exit apex 74. Once the bar 44 is past the exit apex 74, the latch movement unit 61 is biased against the latch stop 68.

Figure 5F:
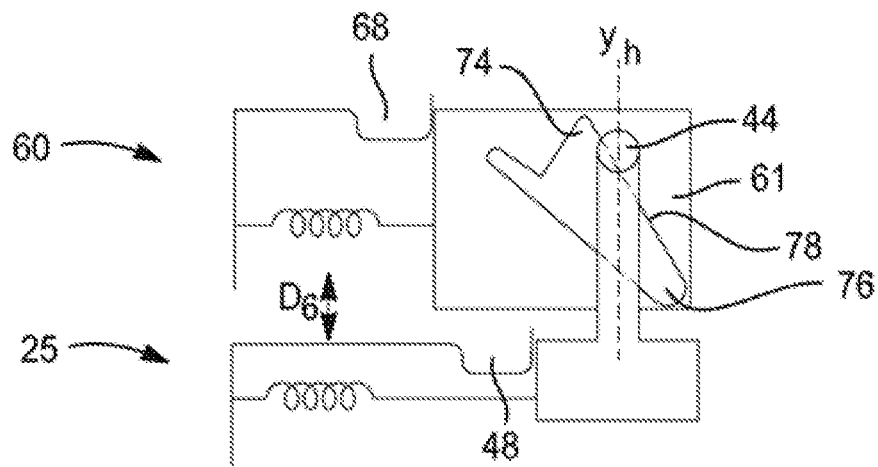
FIG. 5F illustrates the bar extending from the exit apex towards a release apex extending along the return portion.

In FIG. 5F the gap between the movement unit 25 and the latch unit 60 is increased to a distance $D_6$ causing in the bar 44 to slide from the exit apex 74 toward the release apex 76 along the return portion 78. As the bar 44 moves past the exit apex 74 the latch movement unit 61 moves back against the latch stop 68 and the latch movement unit 61 reaches a steady state. As the bar 44 slides along the return portion 78, the bar 44 aligns with a home position axis $y_h$, at which point the movement unit 25 and the latch unit 60 are completely biased against the bar stop 48 and the latch stop 68, respectively, and the movement unit 25 and the latch unit 60 are in a steady state.

Figure 5G:
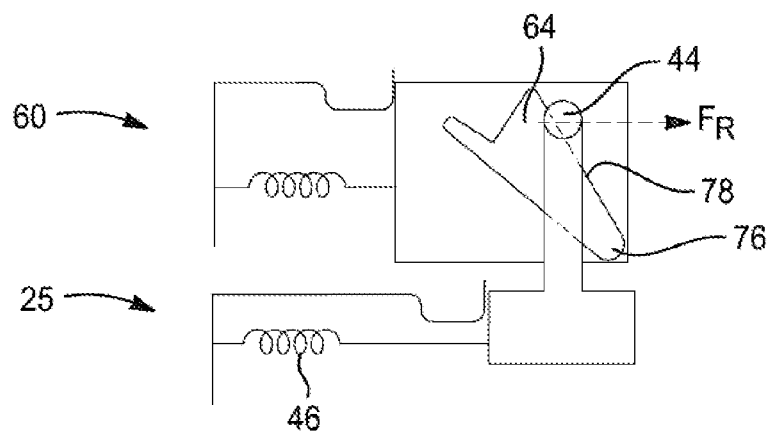
FIG. 5G illustrates the bar extending from the exit apex towards a release apex.

In FIG. 5G, the movement unit 25 and the latch unit 60 are further biased away from each other. Once the bar 44 is past the home position axis (not shown), the hook latch 64 exerts a return force $F_R$ on the bar 44 as the bar 44 slides along the return portion 78 toward the release apex 76. The return force $F_R$ is translated into a higher energy state of the bar biasing member 46.

Figure 5H:
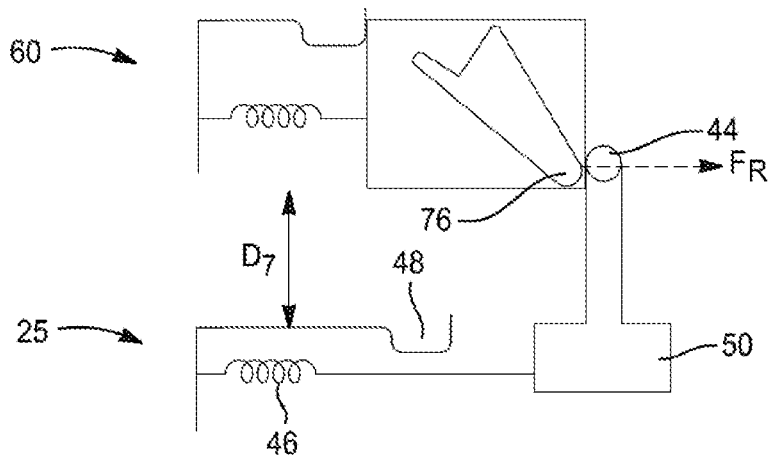
FIG. 5H illustrates the bar located at the release apex with the bar movement unit moving away from the bar stop.

In FIG. 5H, the gap between the movement unit 25 and the latch unit 60 is increased to a distance D7, which results in the latch unit 60 applying a return force $F_R$ on the bar 44 during the travel of the bar 44 toward the release apex 76. The return force $F_R$ is translated into a higher energy state of the bar biasing member 46, resulting in the bar movement unit 50 biasing away from the bar stop 48.

Figure 5I:
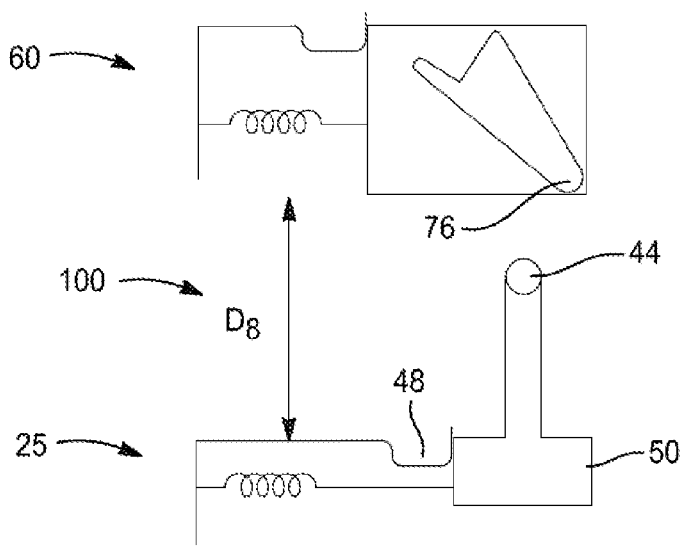
FIG. 5I illustrates both the movement unit and the latch unit in a home position once the movement unit separates from the latch unit.

In FIG. 5I the gap between the movement unit 25 and the latch unit 60 increases to a distance D8, whereby the movement unit 25 and the latch unit 60 come to rest in the home position 100. Upon the bar 44 moving past the release apex 76, the bar movement unit 50 is biased against the bar stop 48.

Figure 6:
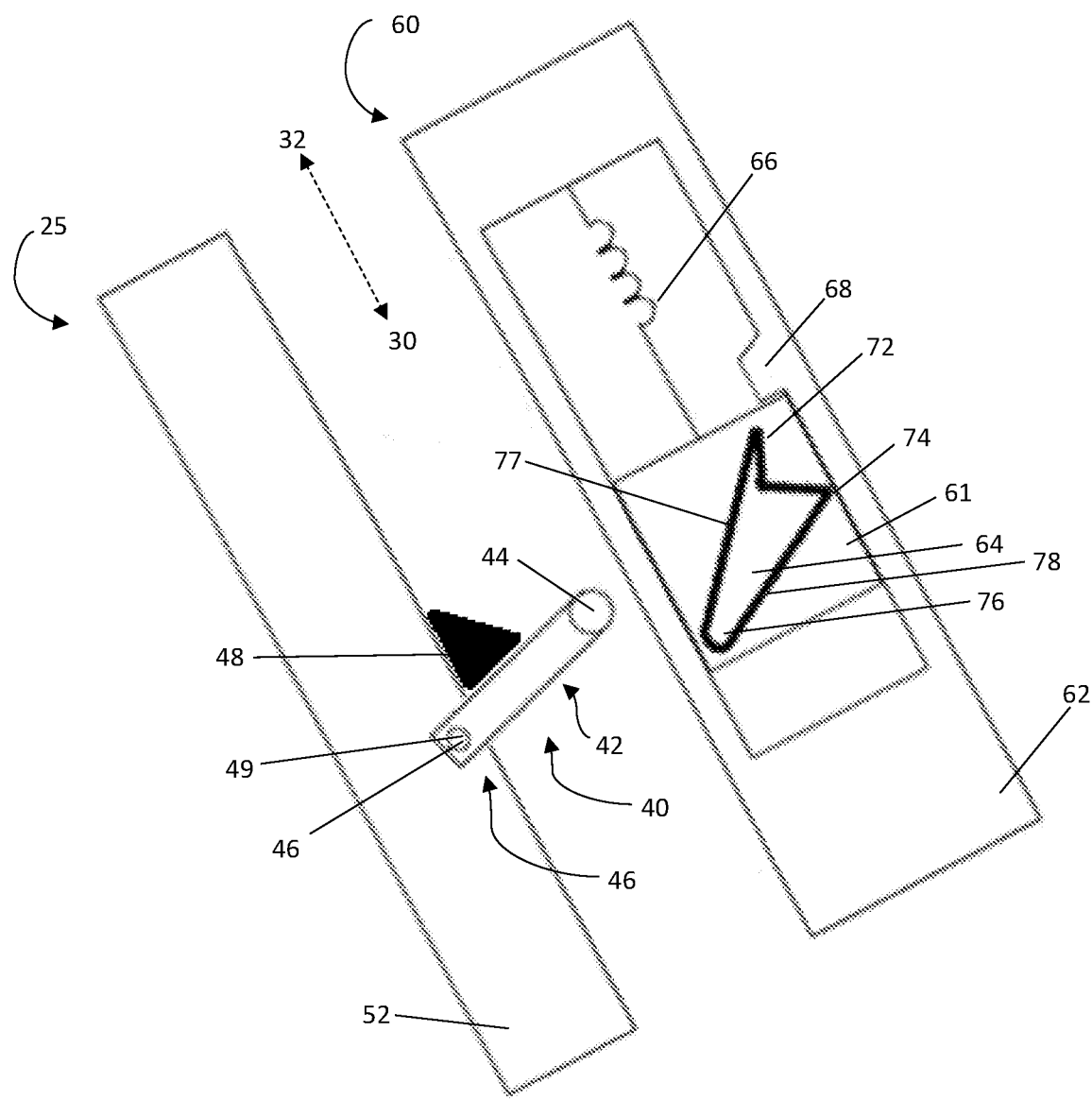
FIG. 6 is a top view of the movement unit and the latch unit with the movement unit being rotatable about an axis.

FIG. 6 is a close-up view of the movement unit 25 and the latch unit 60. The movement unit 25 includes a bar unit 40 connected to a bar frame 52 and a stop 45. The stop 45 impedes the bar arm 42 from movement in the direction of negative bias 32. The bar unit 40 includes the bar biasing member 46, a pivot 49, the bar arm 42 and the bar 44. The latch unit 60 includes the latch unit frame 62 within which the latch movement unit 61 moves in the direction of positive bias 30 or the direction of negative bias 32. The latch biasing member 66 connects the latch movement unit 61 to the latch unit frame 62. When the latch movement unit 61 is biased so as to rest against the latch stop 68, the latch biasing member 66 exerts a constant load on the latch movement unit 61 the direction of negative bias 32. The latch movement unit 61 includes the hook latch 64 that includes the entry apex 72, the exit apex 74, the release apex 76, the entry portion 77, and the return portion 78. The action of the movement unit 25 and the latch unit 60 is analogous to the series shown in FIGS. 5A-5I, above, except that upon the bar 44 moving along the return portion 78 toward the release apex 76, the bar arm 42 pivots about the pivot 49 toward the direction of positive bias 30.

FIGS. 7A-7D are close up views of the movement unit 25 and the latch unit 60, in a series displaying the locking and unlocking action of the movement unit 25 and the latch unit 60.

Figure 7A:
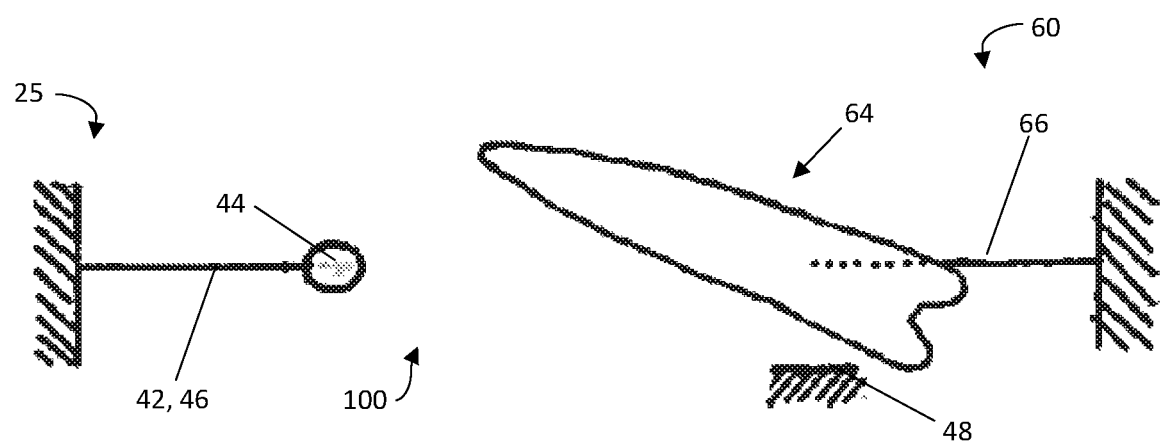
FIG. 7A is a top view of a movement unit and a latch unit in a home position.

FIG. 7A illustrates a latch unit 60 in a home position 100 before a bar 44 of a movement unit 25 is moved by a forward stroke and extends into contact with the latch unit 60. The bar 44 is connected to a bar arm 42, which is also a bar biasing member 46. The bar biasing member 46 is shown in a zero bias state (e.g., home position) and the latch biasing member 66 is shown in a zero bias state (e.g., home position). The bar stop 48 is in-plane with a portion of the movement unit 25 but out-of-plane with the hook latch 64.

Figure 7B:
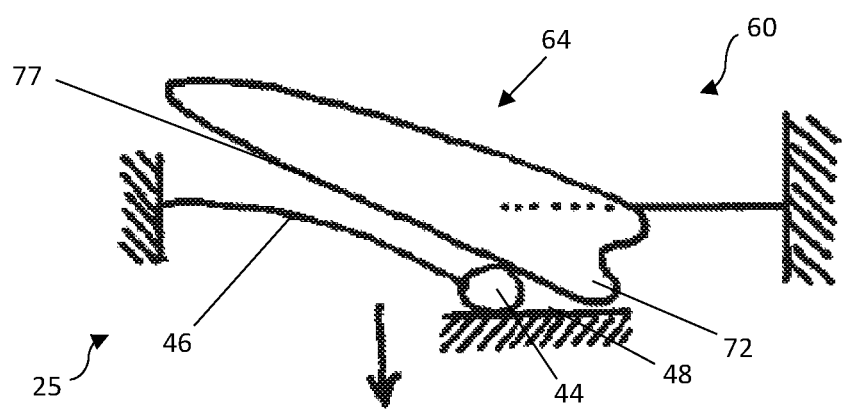
FIG. 7B illustrates a bar being deflected by the hook latch into contact with a stop as the bar moves along a hook latch towards a locked state.

In FIG. 7B, a forward stroke moves the movement unit 25 and it's associated component toward the latch unit 60 and the bar 44 contacts and slides along the entry portion 77 of the hook latch 64 toward the entry apex 72 of the hook latch 64. As the bar 44 slides toward the entry apex 72, the bar biasing member 46 biases downward (e.g., a first direction) into contact with the bar stop 48.

Figure 7C:
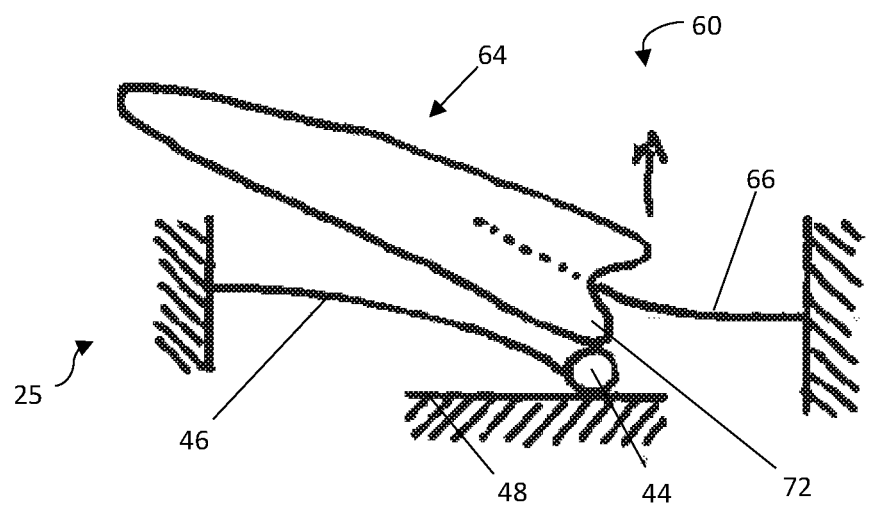
FIG. 7C illustrates a bar located between and in contact with a stop and an entry apex of a hook latch so that the hook latch is deflected away from the stop.

In FIG. 7C, the forward stroke moves the movement unit 25 further toward the latch unit 60 and the bar 44 biases the hook latch 64 upward (e.g., a second direction) as the bar 44 reaches the entry apex 72. The bar biasing member 46 is prevented from deflecting by the bar stop 48 and a load is applied to the hook latch 64 so that the latch biasing member 66 deflects and the hook latch 64 is biased upward.

Figure 7D:
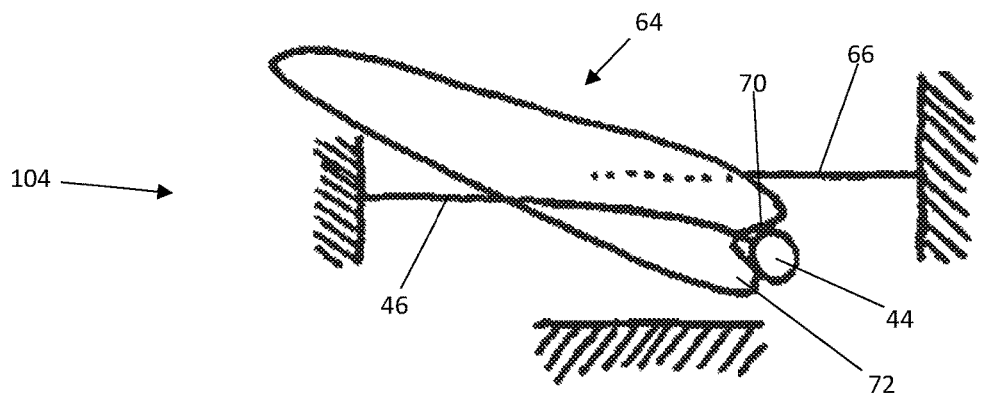
FIG. 7D illustrates a locked state with the bar in a pocket of the hook latch.

In FIG. 7D, the forward stroke has moved the bar 44 past the entry apex 72 where some of the energy stored in the bar biasing member 46 and the latch biasing member 66 are released so that the bar 44 is biased to sit in the pocket 70 of the hook latch 64. The bar biasing member 46 is in the locked position 104.

Figure 7E:
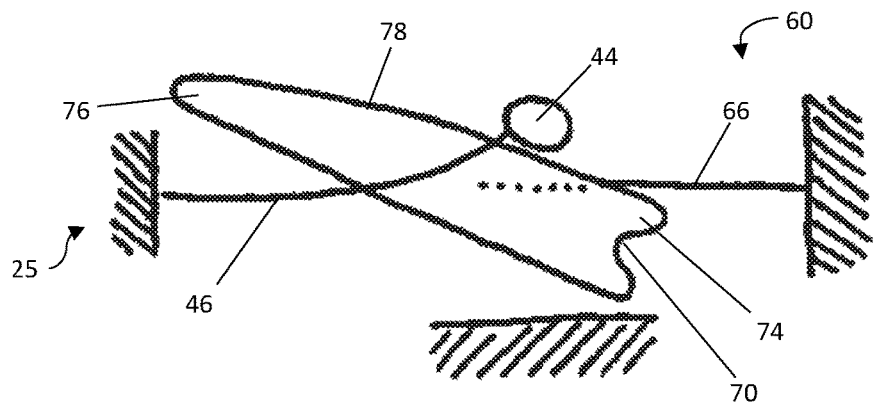
FIG. 7E illustrates the bar after the bar exited the pocket by extending around the exit apex towards the release apex.

FIG. 7E, shows the bar 44 after the bar 44 is released from the pocket 70. To release the bar 44 the movement unit 25 is moved in a forward stroke away from the pocket 70 resulting in the bias in the bar biasing member 46 being released so that the bar 44 moves around the exit apex 74. Once the bar 44 moves out of the pocket 70 and past the exit apex 74 the movement unit 25 can move in a return stroke away from the latch unit 60. The bar 44 is then moved along the return portion 78 where the bar biasing member 46 is biased upward as the bar 44 moves toward the release apex 76. As shown, the latch biasing member 66 remains in a state of zero bias, however, the latch biasing member 66 may be biased downward.

Figure 7F:
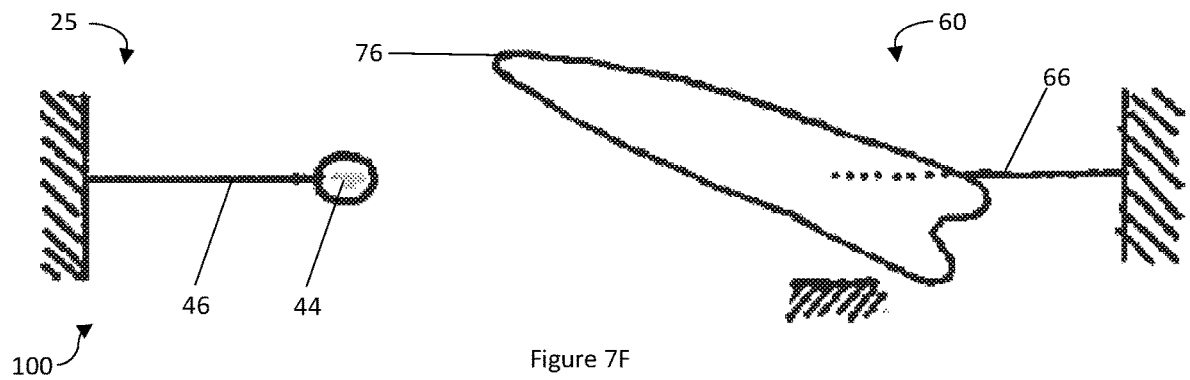
FIG. 7F illustrates the movement unit and the latch unit in a home position.

In FIG. 7F, a return stroke moves the movement unit 25 away from the latch unit 60 and the movement unit 25 comes to rest at the home position 100 after the bar 44 moves around the release apex 76. In the home position 100, the bar biasing member 46 is in a zero bias state and the latch biasing member 66 is in a zero bias state.

Figure 8A:
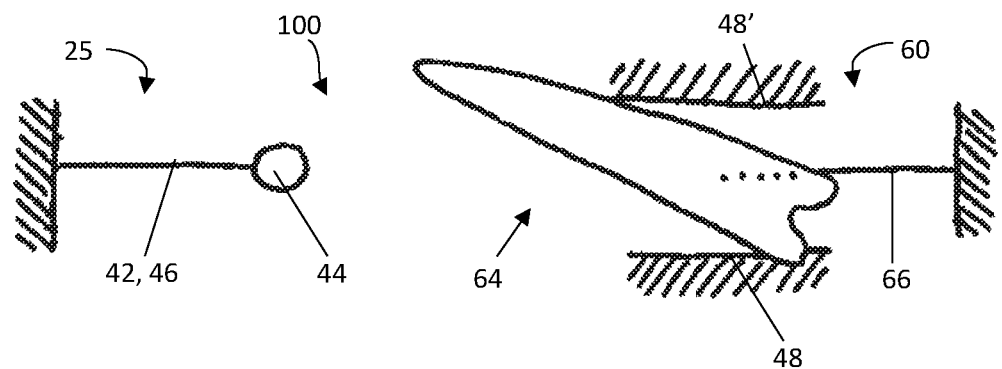
FIG. 8A illustrates a movement unit and a latch unit, in a home position, with two opposing stops.

FIG. 8A illustrates a movement unit 25 and a latch unit 60 in their respective home positions 100. The movement unit 25 includes a bar 44 that is connected to a bar biasing member 46 which is also a bar arm 42. The bar biasing member 46 is in a zero bias state and the latch biasing member 66 is in a zero bias state. The stops 48, 48' are in-plane with the bar 44 but out-of-plane with the hook latch 64 so that the hook latch 64 when deflected can extend past the stops 48, 48'.

Figure 8B:
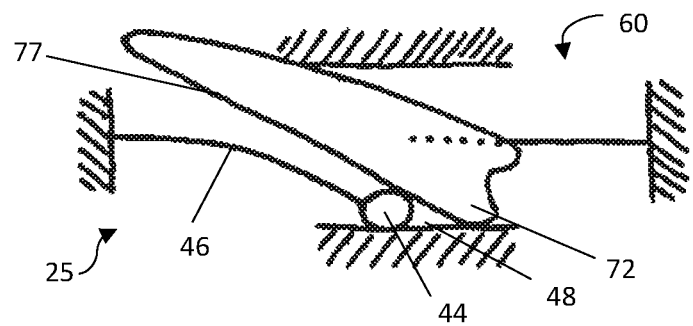
FIG. 8B illustrates the bar being deflected by the hook latch into contact with a first stop as the bar moves along the hook latch towards a locked state.

In FIG. 8B, a forward stroke moves the movement unit 25 toward the latch unit 60 so that the bar 44 contacts and slides along the entry portion 77 toward the entry apex 72. As the bar 44 slides toward the entry apex 72, the bar biasing member 46 biases the bar 44 downward into contact with the bar stop 48, preventing further bias of the bar biasing member 46.

Figure 8C:
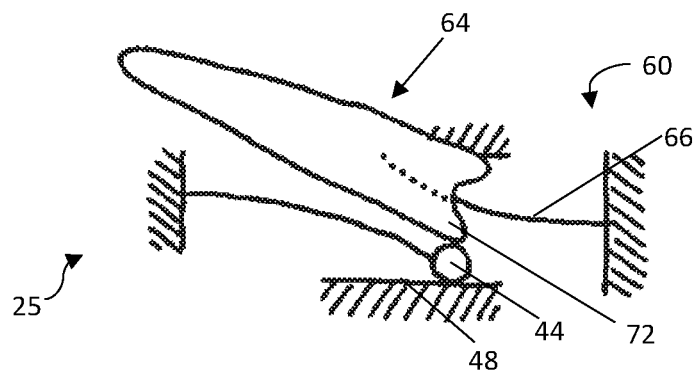
FIG. 8C illustrates the bar located between and in contact with a first stop and an entry apex of the hook latch so that the hook latch is deflected away from the first stop.

In FIG. 8C, the forward stroke moves the movement unit 25 further toward the latch unit 60 and the bar 44 remains in contact with the bar stop 48 and biases the hook latch 64 upward as the bar 44 extends towards and reaches the entry apex 72. The latch biasing member 66 increases in bias as the bar 44 biases the hook latch 64 upward.

Figure 8D:
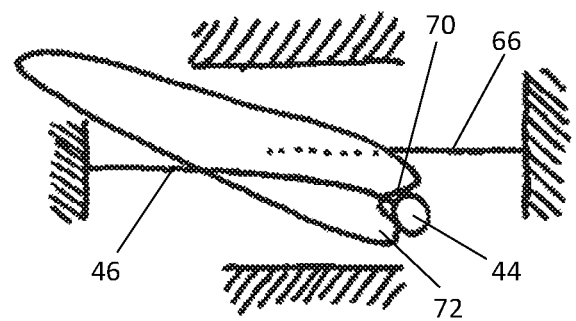
FIG. 8D illustrates the movement unit and the latch unit in the locked state.

In FIG. 8D, the bar 44 has moved past the entry apex 72 where the bar bias member 46 and the latch biasing member 66 release some bias so that the bar 44 is biased towards and sits in the pocket 70. The bar biasing member 46 retains some bias and is slightly biased downward while the latch biasing member 66 moves to a zero bias state.

Figure 8E:
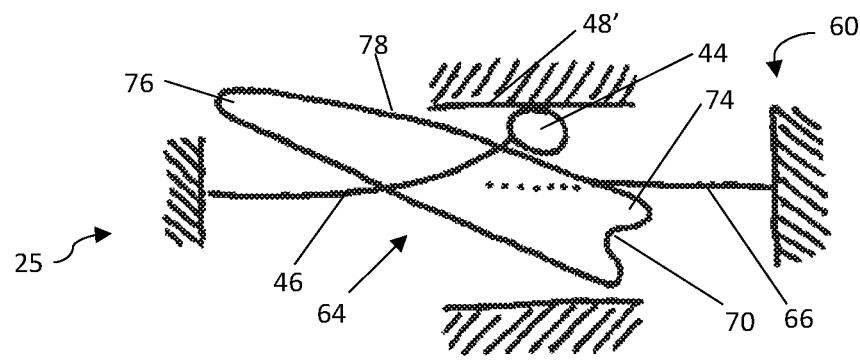
FIG. 8E illustrates the bar after the bar exited the pocket by extending around the exit apex towards the release apex with the bar in contact with the second stop.

FIG. 8E shows the bar 44 after the bar 44 is released from the pocket 70. To release the bar 44 the movement unit 25 is moved in a forward stroke away from the pocket 70 resulting in the bias in the bar biasing member 46 being released so that the bar 44 moves around the exit apex 74. Once the bar 44 moves past the exit apex 74 the movement unit 25 can move in a return stroke away from the latch unit 60. During a return stroke, the bar 44 moves along the return portion 78 of the hook latch 64 and the bar biasing member 46 is biased upward toward the release apex 76. The upward bias of the bar 44 terminates when the bar 44 reaches the upper bar stop 48'.

Figure 8F:
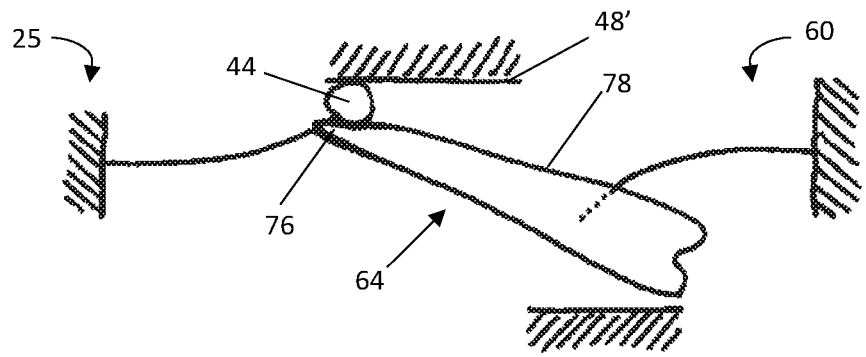
FIG. 8F illustrates the bar located between the second stop and the hook latch so that both the movement unit and the latch unit are deflected.

In FIG. 8F, a return stroke continues and the movement unit 25 moves away from the latch unit 60 while the bar 44 moves along the return portion 78 toward the release apex 76. As shown, upward movement of the bar 44 is restricted by the upper bar stop 48' and the bar 44 is located between the upper bar stop 48' and the hook latch 64. Continued movement of the bar 44 by a return stroke biases the hook latch 64 downward away from the upper bar stop 48'.

Figure 8G:
FIG. 8G illustrates the movement unit and the latch unit in the home position.

In FIG. 8G, the movement unit 25 moves in a return stroke away from the latch unit 60 and the movement unit 25 and latch unit 60 come to rest at the home position 100. The bar biasing member 46 is in a zero bias state and the latch biasing member 66 is in a zero bias state.

Figure 9A:
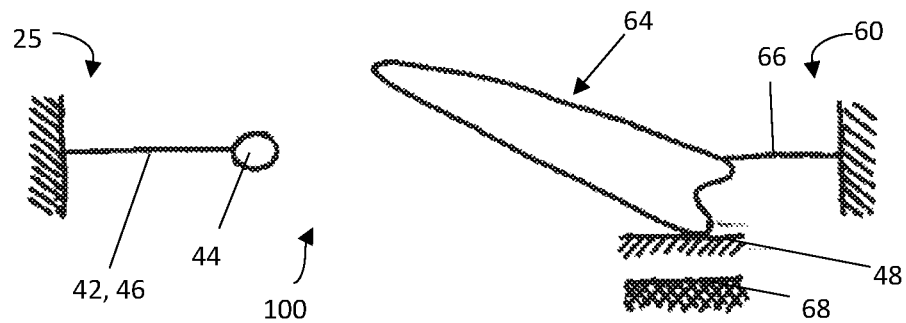
FIG. 9A illustrates the movement unit and the latch unit, in a home position, with two stops located on a same side.

FIG. 9A illustrates a movement unit 25 relative to a latch unit 60 in their respective home positions 100. The movement unit 25 includes a bar 44 that is connected to a bar biasing member 46 which is also the bar arm 42. The bar biasing member 46 is in a zero bias state and the latch biasing member 66 is in a zero bias state. The bar stop 48 is in-plane with the bar 44 but out-of-plane with the hook latch 64 so that the hook latch 64 when deflected can extend past the bar stop 48. The latch stop 68 is in plane with the hook latch 64 but out-of-plane with the bar 44 so that the hook latch 64 when deflected comes into contact with the latch stop 68.

Figure 9B:
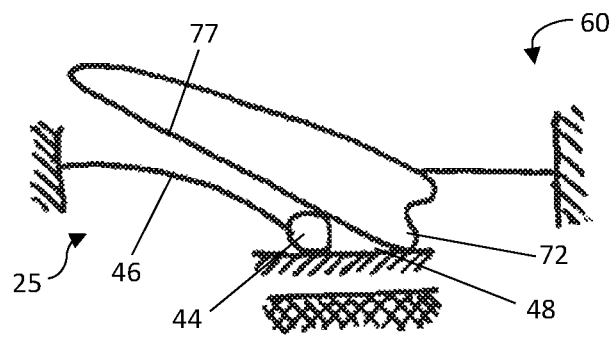
FIG. 9B illustrates the movement unit deflected into contact with a first stop by contact with the hook latch.

In FIG. 9B, a forward stroke moves the movement unit 25 toward the latch unit 60 so that the bar 44 contacts and slides along the entry portion 77 toward the entry apex 72. As the bar 44 slides toward the entry apex 72, the bar biasing member 46 biases downward into contact with the bar stop 48.

Figure 9C:
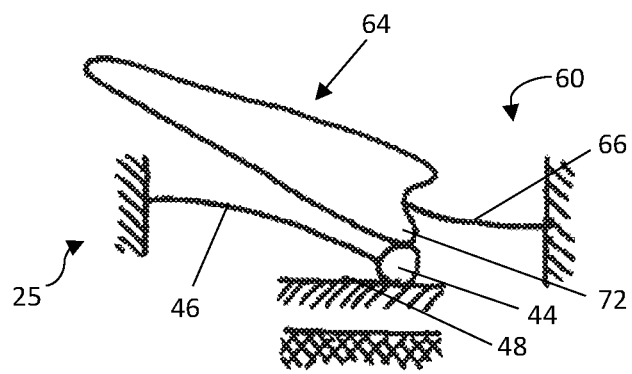
FIG. 9C illustrates the bar located at the entry apex in contact with the first stop and the hook latch so that the latch unit is deflected.

In FIG. 9C, the forward stroke moves the movement unit 25 further toward the latch unit 60 and the bar 44 biases the hook latch 64 upward as the bar 44 extends toward and reaches the entry apex 72. The bar biasing member 46 does not undergo an increase in bias due to the placement of the bar stop 48. The latch biasing member 66 increases in bias as the hook latch 64 is biased upward.

Figure 9D:
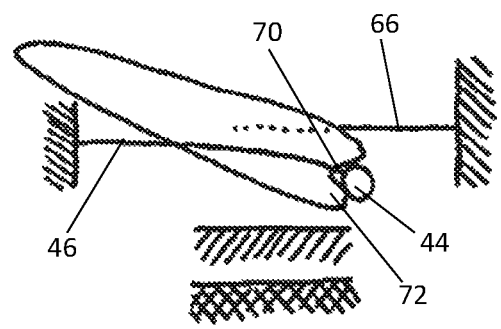
FIG. 9D illustrates the closure assembly in a locked state with the bar being located in the pocket.

In FIG. 9D, the bar 44 has moved past the entry apex 72 where the bar bias member 46 and the latch biasing member 66 release some bias so that the bar 44 is biased towards and sits in the pocket 70. The bar biasing member 46 retains some bias and is slightly biased downward while the latch biasing member 66 moves to a zero bias state.

Figure 9E:
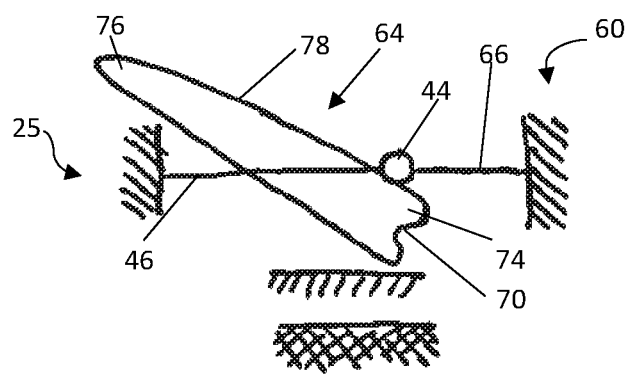
FIG. 9E illustrates the hook latch and the bar both undeflected with the bar moved out of the pocket and around the exit apex.

In FIG. 9E, shows the bar 44 after the bar 44 is released from the pocket 70. To release the bar 44 the movement unit 25 is moved in a forward stroke away from the pocket 70 resulting in the bias in the bar biasing member 46 being released so that the bar 44 moves around the exit apex 74. Once the bar 44 moves past the exit apex 74 the movement unit 25 can move in a return stroke away from the latch unit 60. During a return stroke, the bar 44 moves along the return portion 78 of the hook latch 64 toward the release apex 76. The bar biasing member 46 and latch biasing member 66 achieve a zero bias state.

Figure 9F:
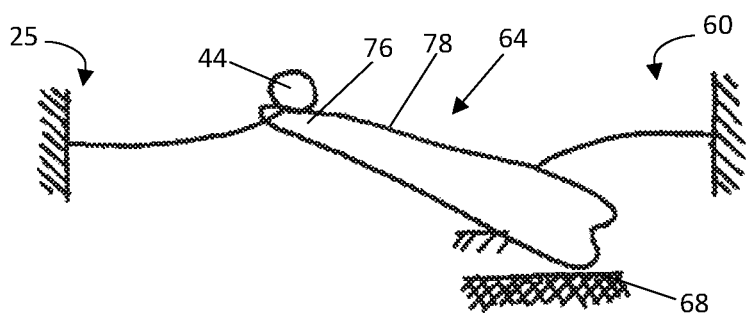
FIG. 9F illustrates the bar extending towards the release apex so that the hook latch is deflected into contact with a second stop and so that the bar is deflected by the hook latch.

In FIG. 9F, a return stroke moves the movement unit 25 away from the latch unit 60 while the bar 44 moves along the return portion 78 toward the release apex 76 and the hook latch 64 is biased downward against a latch stop 68. At the point that the hook latch 64 contacts the latch stop 68, the hook latch 64 is biased upward as the hook latch 64 travels toward the release apex 76.

Figure 9G:
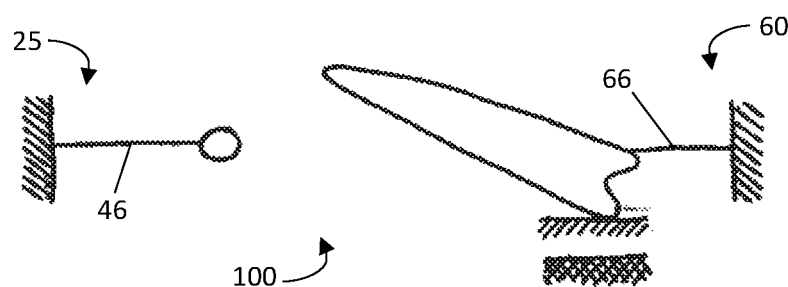
FIG. 9G illustrates the movement unit and the latch unit in the home position.

In FIG. 9G, a return stroke moves the movement unit 25 away from the latch unit 60 and comes to rest at the home position 100. The bar biasing member 46 is in a zero bias state and the latch biasing member 66 is in a zero bias state.

Figure 10:
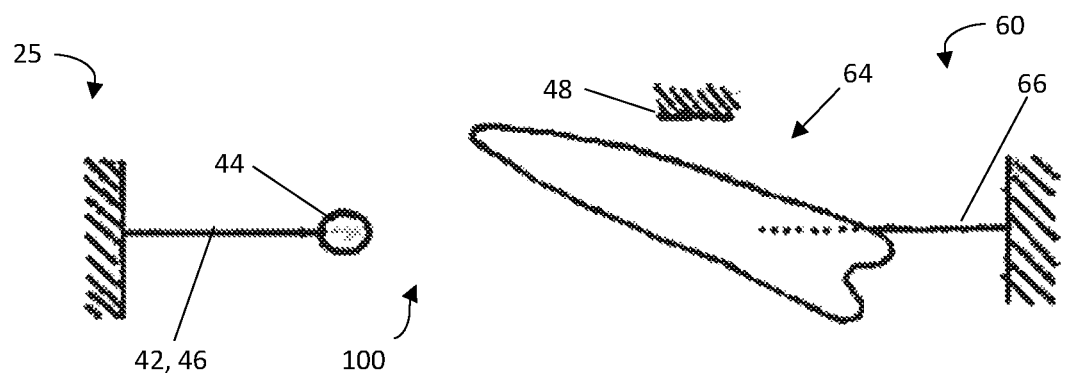
FIG. 10 is a top view of a movement unit and a latch unit in a home position.

FIG. 10 illustrates a latch unit 60 in a home position 100 before a bar 44 of a movement unit 25 is moved by a forward stroke and extends into contact with the latch unit 60. The bar 44 is connected to a bar arm 42, which is also a bar biasing member 46. The bar biasing member 46 is shown in a zero bias state and the latch biasing member 66 is shown in a zero bias state. The bar stop 48 is in-plane with a portion of the movement unit 25 but out-of-plane with the hook latch 64.

Figure 11:
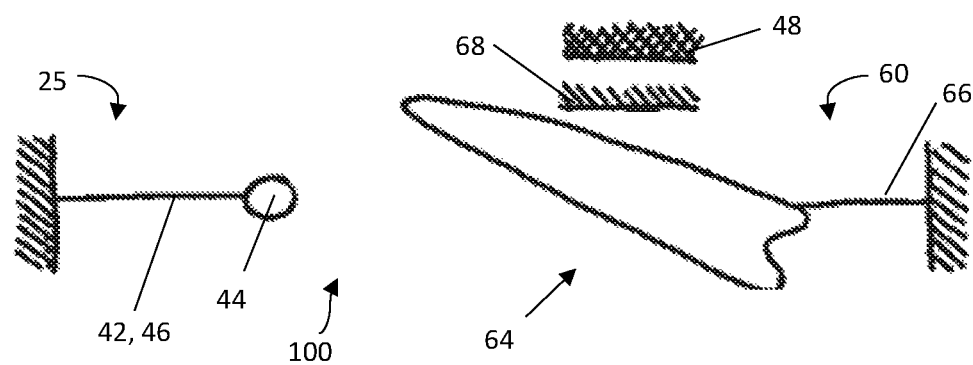
FIG. 11 illustrates the movement unit and the latch unit, in a home position, with two stops located on a same side.

FIG. 11 illustrates a movement unit 25 relative to a latch unit 60 in their respective home positions 100. The movement unit 25 includes a bar 44 that is connected to a bar biasing member 46 which is also the bar arm 42. The bar biasing member 46 is in a zero bias state and the latch biasing member 66 is in a zero bias state. The bar stop 48 is in-plane with the bar 44 but out-of-plane with the hook latch 64 so that the hook latch 64 when deflected can extend past the bar stop 48. The latch stop 68 is in plane with the hook latch 64 but out-of-plane with the bar 44 so that the hook latch 64 when deflected comes into contact with the latch stop 68.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:

1. A surgical device comprising:
   a closure assembly including:
   a. a movement unit configured to be connected to a movable member, the movement unit including:
      i. a bar; and
      ii. a bar biasing member in communication with the movement unit and moving the bar; and
   b. a latch unit configured to be connected to a ground member, the latch unit including:
      i. a hook latch that selectively receives the bar; and
      ii. a latch biasing member in communication with the hook latch to selectively move the hook latch;
   wherein all or a portion of the latch unit is movable relative to the ground member and all or a portion of the movement unit is movable relative to the movable member, and the latch unit and the movement unit are movable relative to each other when the latch unit and the movement unit are in contact;
   wherein the biasing member has a pre-load when the movement unit is in a home position, and the bar is movably mounted to move along a prescribed path so that upon the bar and the hook latch contacting each other, during a process of locking or unlocking, the bar is displaced from a bar home position in a first direction that is transverse to the prescribed path until the bar contacts a bar stop that prevents movement in the first direction, and
   wherein the latch is displaced from a latch home position in a second direction that is transverse to the prescribed path and opposite the first direction.

2. The surgical device of claim 1, wherein the movement unit includes a bar arm connected to the bar, and the surgical device includes the movable member and the bar arm is connected to and movable with the movable member, and along the movable member when the movement unit is moved into contact with the latch unit.

3. The surgical device of claim 1, wherein the movable member moves along a prescribed motion.

4. The surgical device of claim 1, wherein the movement unit includes a bar stop and a bar movement unit, and the bar movement unit is connected to the one or more bars; and
   wherein the bar movement unit and the bar stop are in contact when the movement unit is in a home position.

5. The surgical device of claim 1, wherein the latch unit includes a latch movement unit and a latch stop and the latch movement unit and the latch stop are in contact with the latch unit in a home position.

6. The surgical device of claim 1, wherein a latch movement unit is connected to the latch biasing member, and the latch biasing member has a pre-load when the latch unit is in a home position, and the hook latch is carried on the latch movement unit.

7. A surgical device comprising:
   a closure assembly including:
   b. a movement unit configured to be connected to a movable member, the movement unit including:
      i. a bar; and
      ii. a bar biasing member in communication with the movement unit and moving the bar; and
   b. a latch unit configured to be connected to a ground member, the latch unit including:
      i. a hook latch that selectively receives the bar; and
      ii. a latch biasing member in communication with the hook latch to selectively move the hook latch;
   wherein all or a portion of the latch unit is movable relative to the ground member and all or a portion of the movement unit is movable relative to the movable member, and the latch unit and the movement unit are movable relative to each other when the latch unit and the movement unit are in contact;
   wherein the bar is movably mounted to move along a prescribed path so that upon the bar and the hook latch contacting each other, during a process of locking or unlocking, the bar is displaced from a bar home position in a first direction that is transverse to the prescribed path until the bar contacts a bar stop that prevents movement in the first direction, and
   wherein the hook latch is displaced from a latch home position in a second direction that is transverse to the prescribed path and opposite the first direction.

8. The surgical device of claim 7, wherein the hook latch is displaced from the latch home position in the first direction that is transverse to the prescribed path when the bar contacts the hook latch until the hook latch contacts a latch stop, and
   wherein the bar is displaced from the bar home position in the second direction that is transverse to the prescribed path and opposite the first direction when the hook latch is in contact with the latch stop.

9. The surgical device of claim 7, wherein the bar and the hook latch contact each other a second time, during the process of locking and unlocking, and the bar is displaced from the bar home position in the second direction until the bar contacts a second bar stop that prevents movement of the bar in the second direction, and
   wherein the hook latch is displaced from the latch home position in the first direction when the bar contacts the second bar stop.

10. A surgical device comprising:
    a closure assembly including:
    a. a movement unit configured to be connected to a movable member, the movement unit including:
       i. a bar; and
       ii. a bar biasing member in communication with the movement unit and moving the bar; and
    b. a latch unit configured to be connected to a ground member, the latch unit including:
       i. a hook latch that selectively receives the bar; and
       ii. a latch biasing member in communication with the hook latch to selectively move the hook latch;
    wherein all or a portion of the latch unit is movable relative to the ground member and all or a portion of the movement unit is movable relative to the movable member, and the latch unit and the movement unit are movable relative to each other when the latch unit and the movement unit are in contact;
    wherein the hook latch is movably mounted so that upon the bar and the hook latch contacting each other, during a process of locking of unlocking, the hook latch is displaced from a latch home position in a first direction that is transverse to a prescribed path of the bar until the hook latch contacts a latch stop that prevents movement of the hook latch in the first direction, and
    wherein the bar is displaced from a bar home position in a second direction that is transverse to the prescribed path and opposite the first direction.

11. The surgical device of claim 10, wherein the bar and the hook latch contact each other a second time, during the process of locking and unlocking, and the hook latch is displaced from the latch home position in the second direction where the hook latch contacts a second stop that prevents movement of the hook latch in the second direction, and
wherein the bar is displaced from the bar home position in the first direction when the hook latch contacts the second stop.

12. A surgical device comprising:
a closure assembly including:
 a. a movement unit including:
  i. a bar;
  ii. a bar biasing member in communication with the bar to selectively move the bar; and
  iii. a bar stop that maintains the bar biasing member with a pre-load when the bar is in a home position; and
 b. a latch unit including:
  i. a hook latch that selectively receives the bar;
  ii. a latch biasing member in communication with the hook latch to selectively move the hook latch; and
  iii. a latch stop that maintains the latch biasing member with a pre-load when the hook latch is in a home position;
 wherein the latch unit and the movement unit are movable relative to each other when the latch unit and the movement unit are in contact;
 wherein when the bar is displaced in a first direction by the hook latch, the hook latch remains in the home position.

13. The surgical device of claim 12, wherein a load on the bar biasing member increases above the pre-load as the bar biasing member moves in the first direction.

14. A surgical device comprising:
a closure assembly including:
 a. a movement unit including:
  i. a bar;
  ii. a bar biasing member in communication with the bar to selectively move the bar; and
  iii. a bar stop that maintains the bar biasing member with a pre-load when the bar is in a home position; and
 b. a latch unit including:
  i. a hook latch that selectively receives the bar;
  ii. a latch biasing member in communication with the hook latch to selectively move the hook latch; and
  iii. a latch stop that maintains the latch biasing member with a pre-load when the hook latch is in a home position;
 wherein the latch unit and the movement unit are movable relative to each other when the latch unit and the movement unit are in contact;
 wherein when the hook latch is displaced in a first direction by the bar, the bar remains in the home position.

15. The surgical device of claim 14, wherein a load on the latch biasing member increases above the pre-load as the hook latch moves in the first direction.

16. A surgical device comprising:
a closure assembly including:
 a. a movement unit including:
  i. a bar;
  ii. a bar biasing member in communication with the bar to selectively move the bar; and
  iii. a bar stop that maintains the bar biasing member with a pre-load when the bar is in a home position; and
 b. a latch unit including:
  i. a hook latch that selectively receives the bar;
  ii. a latch biasing member in communication with the hook latch to selectively move the hook latch; and
  iii. a latch stop that maintains the latch biasing member with a pre-load when the hook latch is in a home position;
 wherein the latch unit and the movement unit are movable relative to each other when the latch unit and the movement unit are in contact;
wherein the bar contacts an entry portion of the hook latch moving the hook latch in a first direction and maintaining the bar in the home position or the bar contacts an entry portion of the hook latch moving the bar in a first direction and maintaining the hook latch in the home position.

17. A surgical device comprising:
a closure assembly including:
 a. a movement unit including:
  i. a bar;
  ii. a bar biasing member in communication with the bar to selectively move the bar; and
  iii. a bar stop that maintains the bar biasing member with a pre-load when the bar is in a home position; and
 b. a latch unit including:
  i. a hook latch that selectively receives the bar;
  ii. a latch biasing member in communication with the hook latch to selectively move the hook latch; and
  iii. a latch stop that maintains the latch biasing member with a pre-load when the hook latch is in a home position;
 wherein the latch unit and the movement unit are movable relative to each other when the latch unit and the movement unit are in contact;
wherein the bar contacts a return portion of the hook latch moving the bar in a first direction and maintaining the hook latch in the home position or the bar contacts an entry portion of the hook latch moving the bar in a first direction and maintaining the hook latch in the home position.

18. A surgical device comprising:
a closure assembly including:
 a. a movement unit including:
  i. a bar;
  ii. a bar biasing member in communication with the bar to selectively move the bar; and
  iii. a bar stop that maintains the bar biasing member with a pre-load when the bar is in a home position; and
 b. a latch unit including:
  i. a hook latch that selectively receives the bar;
  ii. a latch biasing member in communication with the hook latch to selectively move the hook latch; and
  iii. a latch stop that maintains the latch biasing member with a pre-load when the latch is in a home position;
wherein the latch unit and the movement unit are movable relative to each other the latch unit and the movement unit are in contact; and
wherein the latch unit includes a bar movement unit that is in direct contact with the bar stop and the bar is connected to the bar movement unit by a bar arm so that the bar extends outside of a movable member and is capable of extending into a ground member.

* * * * *

UNITED STATES PATENT AND TRADEMARK OFFICE
CERTIFICATE OF CORRECTION

PATENT NO. : 10,849,682 B2  
APPLICATION NO. : 15/941590  
DATED : December 1, 2020  
INVENTOR(S) : Mensch et al.

Page 1 of 1

It is certified that error appears in the above-identified patent and that said Letters Patent is hereby corrected as shown below:

On the Title Page

In item (71), in "Applicant", in Column 1, Line 1, delete "INC.," and insert --INC. d/b/a Olympus Surgical Technologies America,-- therefor In item (73), in "Assignee", in Column 1, Line 1, delete "Inc.," and insert --Inc. DBA Olympus Surgical Technologies America,-- therefor In the Claims In Column 33, Line 63, in Claim 7, delete "b." and insert --a.-- therefor In Column 36, Line 63, in Claim 18, after "other", insert --when--

Signed and Sealed this  
Thirteenth Day of April, 2021

Drew Hirshfeld  
*Performing the Functions and Duties of the*  
*Under Secretary of Commerce for Intellectual Property and*  
*Director of the United States Patent and Trademark Office*